US005696263A

United States Patent [19]

Yu et al.

[11] Patent Number: 5,696,263

[45] Date of Patent: Dec. 9, 1997

[54] ANTIVIRAL ACYCLIC PHOSPHONOMETHOXYALKYLSUBSTITUTED ALKENYL AND ALKYNYL PURINE AND PYRIMIDINE DERIVATIVES

[75] Inventors: Kuo-Long Yu, Hamden; Joanne J. Bronson, Madison, both of Conn.; John C. Martin, San Carlos, Calif.

[73] Assignees: Institute of Organic Chemistry and Biochemistry of the Academy of Sciences of the Czech Republic, Czech Rep.; Rega Stichting v.z.w., Belgium

[21] Appl. No.: 350,851

[22] Filed: Dec. 6, 1994

Related U.S. Application Data

[63] Continuation of Ser. No. 777,835, Oct. 11, 1991, abandoned.

[51] Int. Cl.$^6$ .................... A61K 31/675; C07F 9/6561; C07F 9/6506
[52] U.S. Cl. .................................. 544/244; 544/243
[58] Field of Search ........................................... 544/244

[56] References Cited

U.S. PATENT DOCUMENTS

| | | | |
|---|---|---|---|
| 4,659,825 | 4/1987 | Holy et al. | 514/81 |
| 4,724,233 | 2/1988 | De Clercq et al. | 514/81 |
| 5,047,533 | 9/1991 | Reist et al. | 544/244 |
| 5,142,051 | 8/1992 | Holy et al. | 544/243 |

FOREIGN PATENT DOCUMENTS

| | | |
|---|---|---|
| 0 122 614 | 10/1984 | European Pat. Off. |
| 0 144 913 | 6/1985 | European Pat. Off. |
| 146039 | 6/1985 | European Pat. Off. |
| 0 269 947 B1 | 6/1988 | European Pat. Off. |
| 2125964 | 3/1984 | United Kingdom |
| 2134907 | of 0000 | United Kingdom |
| WO/84/04748 | of 0000 | WIPO |

OTHER PUBLICATIONS

Lal, JCS Perkins 1, p. 1993 (1992).
Holy et al, Coll. Czech. Chem. Comm. 54, 446 (1989).
Connolly, Antimicrobial Agents & Chemotherapy 36, pp. 245–254 (Feb. 1992).
Mansuri, Chem tech, Sep. 1992, p. 564.
Saari, J Med Chem 35, 3792–3802 (1992).
Merck Standby Statement of Sep. 14, 1993.
Anti viral Agents Bulletin 6, p162–163 (Jun. 1993).
Flexner, Anti microbial Agents & Chemotherapy 35, 2544 (Dec. 1991).
Antiviral Agents Bulletin 6, 231 (Aug. 1993).
Saunders, Drug Design and Discovery 8, 255 (1992).
Antiviral Agents Bulletin 6, 228 (Aug. 1993).
Staal, AIDS Research and Human Retroviruses 9, 299 (1993).
De Clerq, AIDS Research and Human Retroviruses 8, 119 (1992).
Jun. 19, 1990 Letter of Dr Eric Sandström.
Rosowsky et al., "Synthesis of 3'-O-Propargylthymidine as a Candidate Antiretroviral Agent," NUCLS & NUCLT 8(4):491–497 (1989).

Abstract for USSR 1,089,093 (Apr. 30, 1984).
Gao et al, J.A.C.S. 109,. 1275–1278 (1987).
Abstract for Gupta et al. Ind. J. Chem Soc (B) 20, 7, p534 (1981).
Abstract for Saxena, Ind. J. Chem Soc (B) 19, 4, p332 (1980).
Abstract for Kos, J. Organic Chem. 48(8), 1207 (1983).
Chu et al, "Chemistry and Antiviral Activities of Acyclonucleosides," J Het Chem 23:289–319 (1986).
De Clercq et al., "Efficacy of Phosphonylmethoxyalkyl Derivatives of Adenine in Experimental Herpes Simplex Virus and Vaccinia Virus Infections in Vivo," Antimicro AG & Chemo 33(2):185–191 (1989).
Holy et al., "Synthesis of (3–Hydroxy–2–Phosphonylmethoxypropyl) Derivatives of Heterocyclic Bases," Collect Czech Chem Commun 54:2470–2501 (1989).
Holy et al., "Synthesis of Isomeric and Enantiomeric O–Phosphonylmethyl Derivatives of 9–(2,3–Dihydroxypropyl) adenine," Collect Czech Chem Commun 54:2775–2791 (1987).
Joshi et al., "Ozonolysis of 6–N–Benzoyl–9–(5–deoxy–2, 3–O–isopopylidene–beta–D–erythro–pent–4–enofuranosyl) adenine and Related Compounds," Tet Lett 34(36):5807–5810 (1993).
Terry et al., "Broad–spectrum antiviral activity of the acyclic guanosine phosphonate (R,S)–HPMPG," Antiviral Res 10:235–252 (1988).
Translation of Czech application "PV 2047–90".
Prisbe, et al., J. Med. Chem., 29:671 (1986).
DeClercq, et al., Nature, 323:464–467 (1986).
DeClercq, E., Antiviral Res., 12:1 (1989).
Holy, et al., Nucl. Acids Res., Symposium Series 14, pp. 277–278 (1984).
Translation of Czech 263951.
Translation of Czech 263952.
De Clercq et al., "Antiviral activity of phosphonylmethoxyalkyl derivatives of purine and pyrimidines," Antiviral Res 8:261–272 (1987).
Harrison et al, "Compendium of Organic Synthetic Methods," pub. John Wiley & Sons pp. 86–87 (1971).
Holy et al., "Phosphonylmethyl Ethers of Nucleosides and Their Acyclic Analogues," Am Chem Soc 4:51–71 (1989).
House, Herbert O., "Modern Synthetic Reactions, 2nd ed.," The Benjamin/Cummings Publishing Company pp. 19, 49–57 (1972).

(List continued on next page.)

*Primary Examiner*—Mark L. Berch
*Attorney, Agent, or Firm*—Max D. Hensley

[57] ABSTRACT

Compounds are provided that generally have the structure $BCH_2CH(R)OCH_2P(O)(OH)_2$, wherein B is a purinyl or pyrimidinyl base and R is $C_{1-2}$ alkyl substituted with azido or amino, straight or branched alkenyl of 2–6 carbon atoms or alkynyl of 2–6 carbon atoms, together with the monester and diesters of such compounds with a $C_{1-5}$ alkanol, and the corresponding salts, hydrates, solvates, the (R) or (S) isomers and the racemic (RS) mixtures thereof. The compounds have desirable antiviral activity.

14 Claims, 7 Drawing Sheets

OTHER PUBLICATIONS

March, Jerry, "Advanced Organic Chemistry," pub. John Wiley & Sons p. 329 (1985).

Mazur et al., "Isosteres of Natural Phosphates. 11. Synthesis of a Phosphonic Acid Analogue of an Oligonucleotide," Tet. Lett. 40:3949–3956 (1984).

Pappo et al, "Osmium Tetroxide–Catalyzed Periodate Oxidation of Olefinic Bonds," J. Org. Chem. 21:478 (1956).

Uhlmann et al, "Antisense Oligonucleotides: A New Therapeutic Principle," Chem. Rev. 90:543–584 (1990).

ANTIVIRAL ACYCLIC PHOSPHONOMETHOXYALKYLSUBSTITUTED ALKENYL AND ALKYNYL PURINE AND PYRIMIDINE DERIVATIVES

This is a continuation of application Ser. No. 07/777,835 filed on Oct. 11, 1991 abandoned.

BACKGROUND OF THE INVENTION

1. Field of the Invention

This invention concerns nucleotide analogs, their method of preparation and their compositions and use in the treatment of viral infections. In particular, it concerns acyclic phosphonomethoxyalkylsubstituted, alkenyl and alkynyl derivatives of purine and pyrimidine bases.

2. Information Disclosure Statement

Infectious viral diseases are recognized as an important medical problem. Progress against infectious viral diseases requires the development of drugs with selective antiviral activity while remaining benign to normal cell lines. A number of antiviral agents currently under study, which seem to possess some selectivity, are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid. Effectiveness of these antiviral agents depends on selective conversion by viral enzymes or by host enzymes, to the corresponding nucleotide analog which is then converted to the triphosphate and incorporation into viral nucleic acid occurs. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

Reist and Sturm in PCT/US 84/00737, published Dec. 6, 1984, disclosed new phosphonic acid analogs of nucleoside phosphates which are useful as antivirals for incorporation into viral DNA. The structural formula for these compounds is shown below as 1.

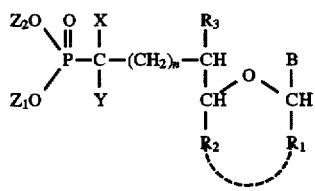

In the Reist compounds, B is a purine or pyrimidine base: $R_1$ and $R_2$ together complete a β-pentofuranose sugar or $R_1$ is H and $R_2$ is H or hydroxymethyl; $R_3$ is H or OH; X is H, OH or together with Y is carbonyl oxygen and Y can also be H; $Z_1$ and $Z_2$ are H or alkyl. These art compounds are generally distinguished from the compounds of the instant invention by 1) the ether-oxygen link to the carbon atom attached to the base which is intended to preserve or mimic the acetal oxygen bond of a pentofuranose sugar ring; and 2) the phosphate modification is a phosphonoalkylene moiety. In contrast, the acyclic sugar analog component of the instant compounds is comprised of an all carbon atom backbone up to a phosphonomethoxy moiety.

Similarly, synthesis and anti-Herpes-Virus activity of phosphate and phosphonate derivatives of 9-[(1,3-dihydroxy-2-propoxy)methyl]guanine (Formula 2) was disclosed by Prisbe, et al., in *J. Med. Chem.*, 1986, 29, 671.

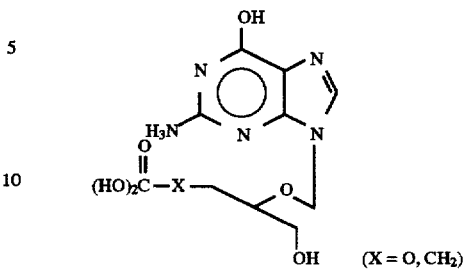

More closely related are adenine phosphonic acid analogs (Formula 3) and their syntheses which were disclosed in the UK Patent Application of Holy, et al., GB 2,134,907A published Aug. 22, 1984.

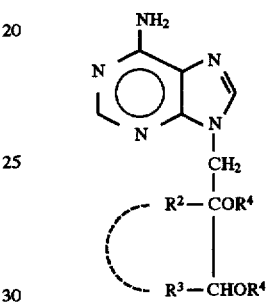

In Formula 3, $R^2$ and $R^3$ are H or together complete a ribonucleoside ring; and both $R^4$ are alternately a hydrogen and —$CH_2P(O)(OH)_2$ group.

A preferred example of one of these compounds, known as (S)-HPMPA (Formula 4) was disclosed by DeClercq, et al., in *Nature*, 1986, 323, pp. 464–467 and earlier by Holy, et al., *Nucleic Acids Research*, Symposium Series No. 14, 1984 pp. 277–278.

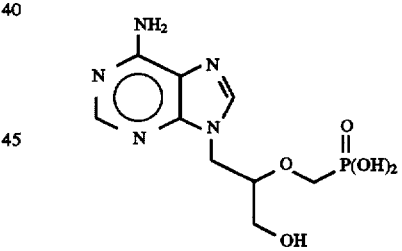

Another closely related group of compounds are 9-(2-phosphonylmethoxyethyl) purines (Formula 5) which were disclosed in Czechoslovakian certificate of Holy et al., certificate No. 263,951. The compound extensively investigated was the adenine derivative, namely PMEA as reported in Czechoslovakian certificate of Holy et all, certificate No. 263,952. Various tests with experimental animals had proven its effect on Moloney sarcoma virus, murine leukemia virus, simian immunodeficiency virus (SIV), and in tissue cultures on HIV as disclosed by E. DeClercq in *Antiviral Res.*, 12, 1 (1989).

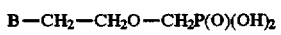

In Formula 5, B denotes a purine-9-yl.

Also a closely related group of compounds is N-(3-fluoro-2-phosphonylmethoxypropyl) derivatives of purine and pyrimidine heterocyclic bases, (Formula 6) their preparation and use, which are disclosed in Czechoslovakian patent application of Holy, et al., PV2047-90, filed Apr. 24, 1990.

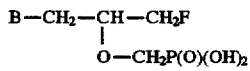
|
O—CH₂P(O)(OH)₂

6

In Formula 6, B denotes purine-9-yl or pyrimidine-1-yl moiety and the absolute configuration at the C-2 carbon atom is S, R or RS. The compounds of Formula 6 shows selective antiretroviral activity.

A. Holy, also discloses the synthesis of the racemic (RS), the (R) and (S) 3'-azidomethyl and 3'-aminomethyl adenine analogs of HPMPA in *Collect. Czech-Chem. Commun*, 54, 446 (1989).

There is no teaching contained in these references or a suggested combination thereof, which would make obvious the compounds, their preparation, and their composition and use of the present invention.

SUMMARY OF THE INVENTION

Phosphonomethoxyalkenyl and azidoalkyl purine and pyrimidine derivatives have been synthesized and found to possess useful antiviral activity.

The alkynyl nucleotide analogs of purines and pyrimidines can be prepared by following the same synthetic sequence which is used for the preparation of the alkenyl derivatives. The aminoalkyl derivatives can be prepared by reduction of the corresponding azidoalkyl derivatives. These compounds differ from the natural nucleotides by having structural variations in their sugar analog component which can be accompanied by variation in their nucleotide base moiety also. Additionally, these compounds differ from the naturally occurring phosphate structure of nucleotides by nature of the oxygen-carbon-phosphorous bonds in these phosphonomethoxy derivatives. The compounds of the present invention are represented by the structural Formula I,

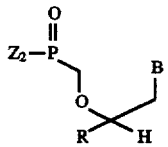

I wherein B is a purine or pyrimidine base; and R is straight alkyl substituted by azido or amino, wherein the alkyl is from 1–2 carbon atoms, straight or branched alkenyl or alkynyl of 2–6 carbon atoms. Other aspects of this invention involve preparation of these compounds, their formulation into pharmaceutical compositions and the use of these formulations to treat viral infections in mammals including humans and in particular, those caused by HIV.

DETAILED DESCRIPTION OF THE INVENTION

Figure 1:
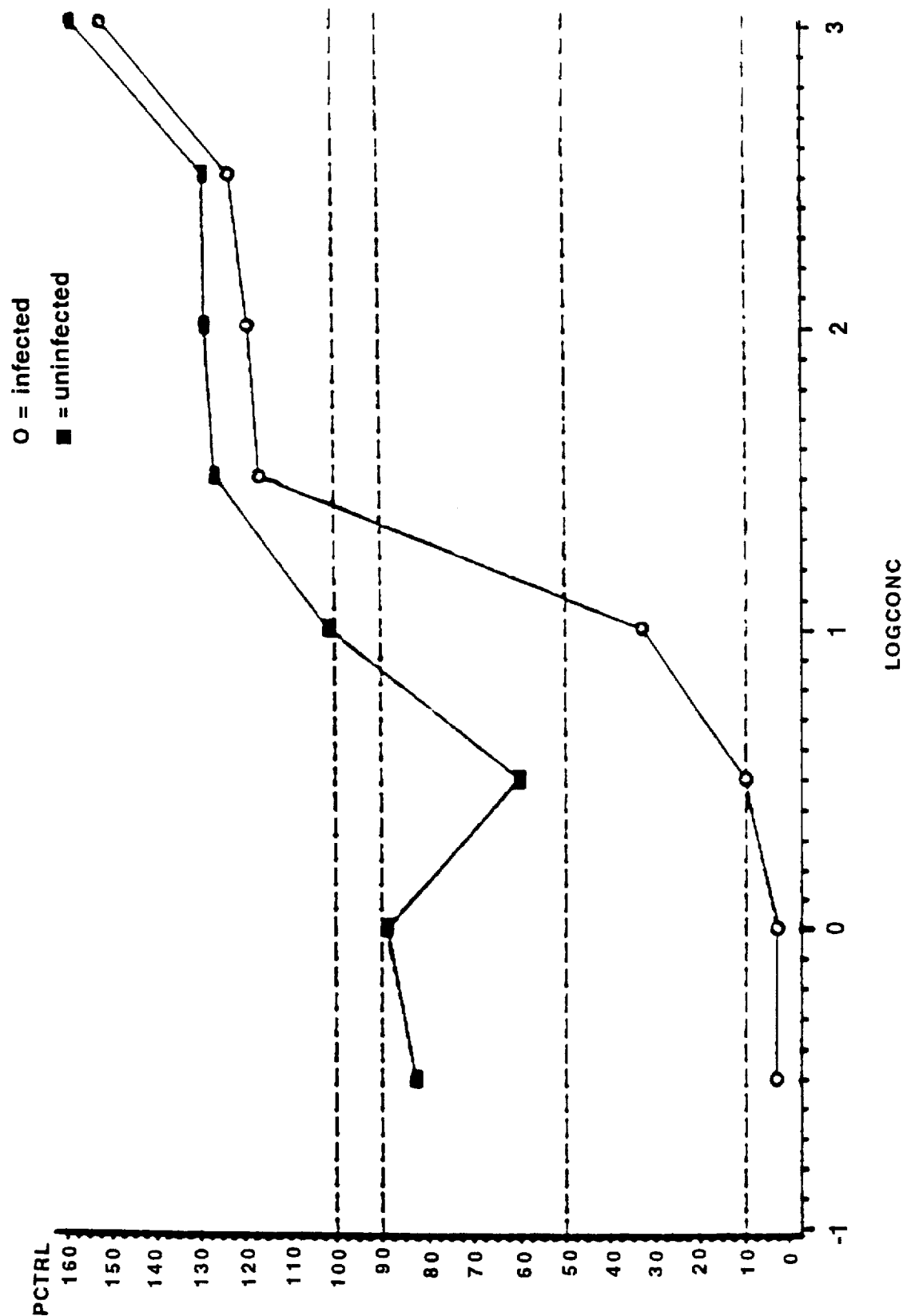

The compounds of this invention are phosphonomethoxyalkylsubstituted, alkenyl or alkynyl purine and pyrimidine derivatives of Formula I.

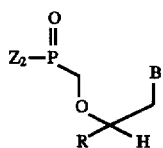

I

In Formula I, B is a purine or pyrimidine base selected from the group consisting of adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, uracil, 5-bromouracil, 5-iodouracil, 5-ethyluracil, 5-propyluracil, 5-vinyluracil, and 5-bromovinyluracil; R is alkyl substituted by azido or amino, wherein the alkyl is from 1–2 carbon atoms, straight or branched alkenyl of 2–6 carbon atoms or a straight or branched alkenyl of 2–6 carbon atoms, the monoester, diester and the corresponding salt, hydrate, solvate, the R or S isomer and the racemic mixture (RS) thereof, with the proviso that when R is azidomethyl or aminomethyl, then B is not adenine and when R is (S) azidomethyl, then B is not thymine and when R is (S) azidoethyl, then B is not guanine.

Examples of alkyl of 1–2 carbons which are substituted by amino or azido are:

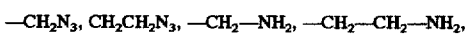

Examples of said alkenyl of 2–6 carbon atoms are:

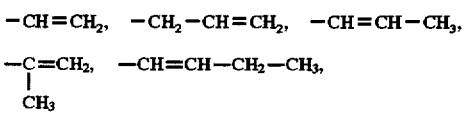

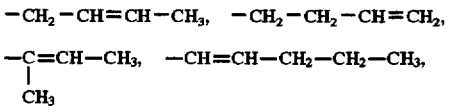

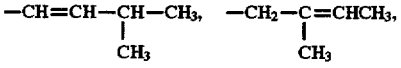

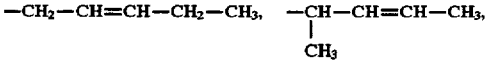

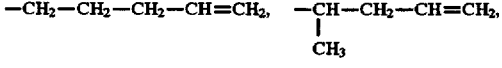

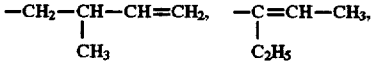

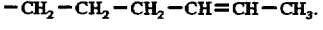

Examples of said alkynyl of 2–6 carbon atoms are:

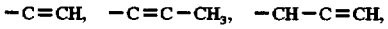

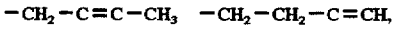

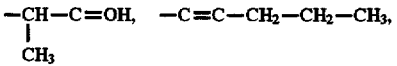

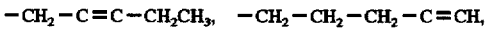

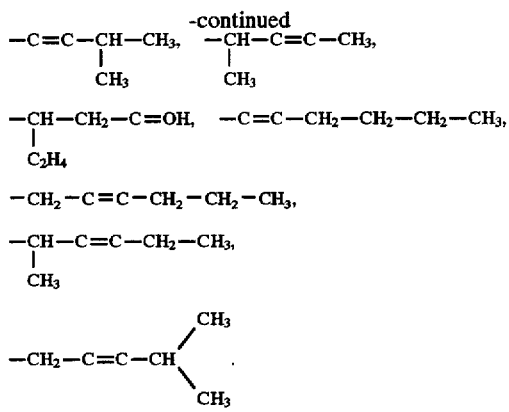

The monoesters and the diesters are of alkanol of 1–5 carbon atoms, as, for example, methanol, ethanol, propanol, isopropanol, butanol, isobutanol, pentanol, etc. The preferred phosphonate moiety are the monoester and the acid.

The salts are pharmaceutically acceptable non-toxic salts. Such physiologically acceptable salts may include those derived by combination of appropriate cations such as alkali and alkaline earth metal ions or ammonium and quaternary amino ions with the acid anion moiety of the phosphonic acid group. Additionally, salts may be formed from acid addition of certain organic and inorganic acids with basic centers of purines and pyrimidines. Such acids are, for example, HCl, HBr, $H_2SO_4$, and organic sulfonic acids and the like. Examples of metal salts are $Li^+$, $K^+$, $Na^+$, $Ca^{++}$ and $Mg^{++}$.

The compounds of the present invention can exist in various tautomeric forms, in their nonionized as well as zwitterionic form and/or in the form of solvates and hydrates, which are to be included within the scope of the present invention. Examples of such solvates are methanolate, ethanolate, propanolate, iso-propanolate, butanolate, etc., and of hydrates are monohydrate, dihydrate, trihydrate, etc.

The compounds of the present invention can exist as optical isomers and both racemic (RS) and the individual chiral isomers R or S are all within the scope of the invention. The preferred isomer is R, which unexpectedly exhibits complete cell protection against HIV over a broad concentration range with no observable cytotoxicity.

The preferred compounds of Formula I are those wherein B is guanine, adenine, uracil or thymine and R is alkyl of 1–2 carbon atoms which is substituted by azido or amino, straight alkenyl or alkynyl of 2–3 carbon atoms. The most preferred compounds of Formula I are those wherein B is guanine, adenine, uracil or thymine and R is $CH_2N_3$, —CH=$CH_2$, —$CH_2$—CH=$CH_2$ or —C≡CH.

The outstanding compounds of Formula I are (R)-9-[2-phosphonomethoxy)-3-butenyl]guanine ((R)-2'-vinyl PMEG) and (R)-[3-azido-2-(phosphonomethoxy)propyl] guanine ((R)-2'-azidomethyl PMEG), which surprisingly and dramatically exhibits cell protection against HIV over a broad concentration with no observable cytotoxicity.

The compounds of Formula I, namely, the (R) and (S) chiral isomers can be prepared by a stero-specific synthesis, beginning with the appropriate enantiomeric (chiral) starting material. The procedure is illustrated in reaction scheme 1 for the (R) isomer. The (S) isomer can be prepared following the reaction scheme 1, except for the use of opposite enantiomeric (chiral) starting material.

The (R) and (S) chiral isomers can also be prepared by resolving the racemic mixture (RS) through well-known techniques, for example, the separation of diastereomeric salts formed with optically active adjuncts, e.g., acids or bases followed by conversion to the (R) and (S) isomer. The racemic mixture (RS) can be prepared using the reaction scheme 1, except for the use of the racemic starting material.

Scheme 1

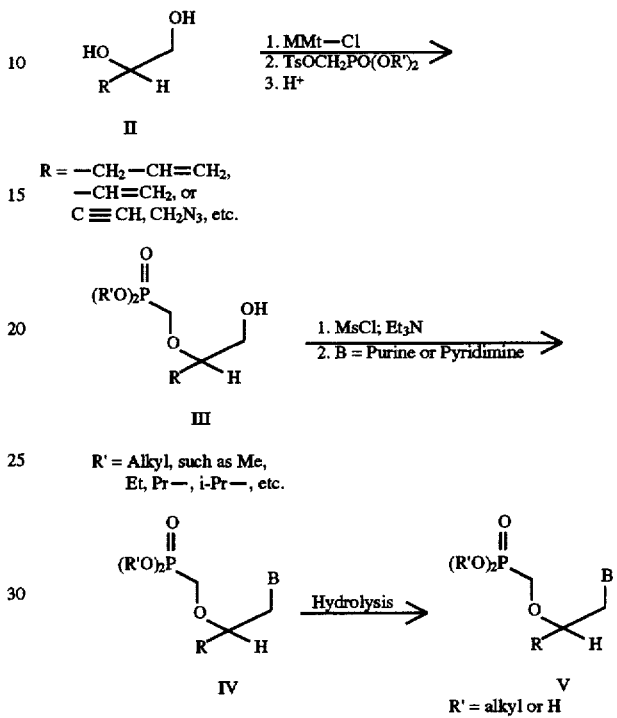

The preparation of the chiral (R)-isomer of Formula I is illustrated in reaction scheme 1 starting with (R)-1,2-propanediol of Formula II. The 1,2-propanediol of Formula II can be synthesized following procedures known in the art with commercially available starting materials. The primary alcohol of Formula II can be selectively protected with p-anisylchlorodiphenylmethane (MMt-Cl) in the presence of dimethylaminopyridine and triethylamine to produce the corresponding ether, which can then be alkylated with diisopropyl tosyloxymethanephosphonate to give the corresponding phosphonate ester. The phosphonate ester can then be hydrolyzed with acid to remove the ether group to produce the compound of Formula III. The primary alcohol of Formula III can be converted to an organic leaving group such as halide, tosylate, mesylate and triflate in the presence of an organic base. Advantageously the reaction can be carried out with methylsulfonyl chloride and triethylamine to produce the corresponding mesylate. The condensation of purine or pyrimidine base can be carried out in a coupling reaction with the mesylate in an inert organic solvent such as acetonitrile, dimethylformamide and the like in the presence of an excess of inorganic bases such as cesium carbonate or sodium hydride to produce the compound of Formula IV. The compound of Formula IV may be first treated with bromotrimethylsilane and then hydrolyzed in an acidic medium, for example, 2N hydrochloric acid, to produce the optically active (R)-isomer of Formula I. The compound of Formula IV can be hydrolyzed with alkali to give the corresponding monoesters of Formula V.

The preparation of the chiral (S)-isomer of Formula I starts with the (S)-1,2-propanediol which is commercially available or can be synthesized following procedures known in the art with commercially available starting materials. The optically active (S)-isomer of Formula I can be prepared from the primary alcohol following the same general procedures and reaction sequences as illustrated in reaction scheme 1 for the preparation of the (R)-isomer of Formula I. The racemic mixture (RS) of the compound of Formula I can be prepared following the same general procedures and reaction sequences as illustrated in reaction scheme 1 for the preparation of the (R)-isomer of Formula I, but starting with the racemic (RS) 1,2-propanediol of Formula II.

An alternate route for the preparation of (S) and (R) chiral isomers of the compound of Formula I, when R is vinyl is illustrated in reaction scheme 2.

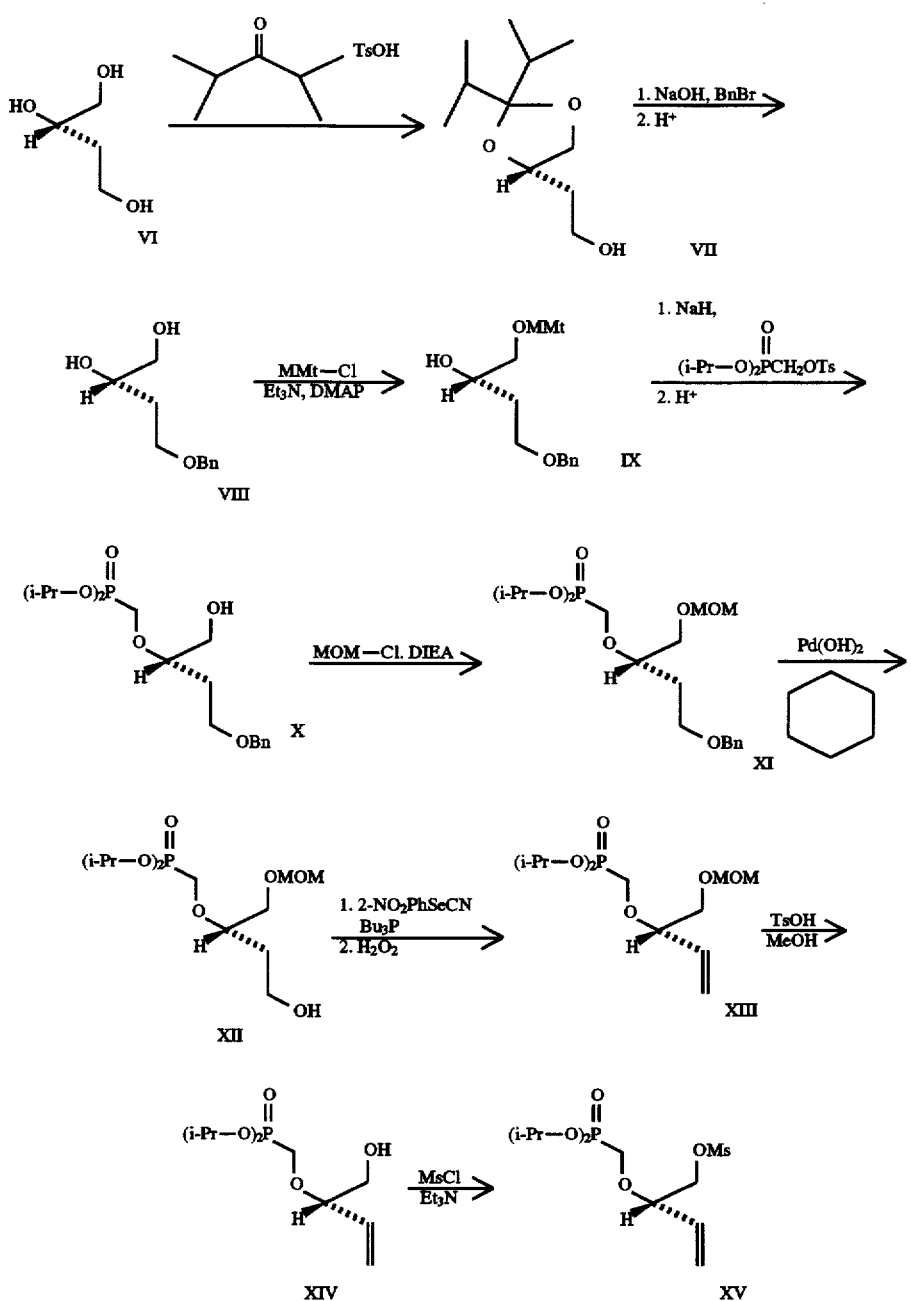

-continued
Scheme 2

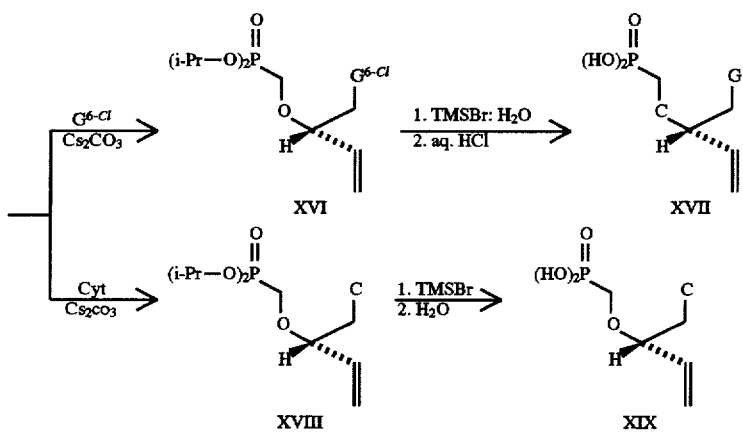

The commercially available chiral (S)-1,2,4-butane triol of Formula VI is converted to (S)-2,2-diisopropyl-4-(2-hydroxyethyl)-dioxolane of Formula VII with 2,4-dimethyl-3-pentanone and P-toluenesulfonic acid in an inert organic solvent, for example, benzene. The dioxolane of Formula VII is converted to (S)-4-O-benzyl-1,2,4-butanetriol of Formula VIII with benzylbromide and tetrabutylammonium iodide in the presence of sodium hydroxide to give the 4-O-benzyl-dioxolane intermediate which is then hydrolized with acid to give the compound of Formula VIII. The primary alcohol of the compound of Formula VIII is selectively protected with P-anisylchlorodiphenylmethane (MMt-Cl) in the presence of dimethylaminopyridine and triethylamine to give the compound of Formula IX. The compound of Formula IX is alkylated with diisopropyl tosyloxymethanephosphonate to give an intermediate which is then hydrolyzed in the presence of an acid to give the compound of Formula X. The primary alcohol of the phosphonate ester of Formula X is protected with chloromethyl methyl ether (MOM-Cl) in the presence of diisopropylethylamine and methylene chloride to produce the compound of Formula XI. The benzyl protecting group of the compound of Formula XI is then selectively removed by catalytic hydrogenolysis using palladium hydroxide on carbon in an organic medium containing cyclohexene and ethanol to produce the compound of Formula XII. The compound of Formula XII is converted to the compound of Formula XIII with 2-nitrophenylselenocyanide and tributylphosphine in anhydrous tetrahydrofuran to give the nitrophenylselenyl intermediate, which is then oxidized with hydrogen peroxide. The compound of Formula XIII is converted to the compound of Formula XIV by hydrolyzing the methoxymethylether group of the compound of Formula XIII with P-toluenesulfonic acid in the presence of an alcohol, such as methanol. The compound of Formula XIV is converted to the mesylate of Formula XV with mesyl chloride in the presence of triethylamine and an inert organic solvent, such as methylene chloride. The mesylate of Formula XV is then coupled with a purine or pyridine base, for example, guanine or cytosine in an inert organic solvent such as acetonitrile, dimethylformamide, and the like in the presence of an excess of inorganic bases, such as cesium carbonate or sodium hydride to produce the compound of Formulae XVI and XVIII. The compounds of Formulae XVI and XVIII are then treated with bromotrimethylsilane and then further hydrolyzed in an acidic medium, for example, 2N hydrochloric acid, to produce the optically active (S)-isomer of Formulae XVII and XIX. The monoesters of Formula XVII and XIX can be prepared by subjecting the compounds of Formula XVI and XVIII to alkline hydrolysis.

The optically active (R) chiral isomer of the compound of Formula I when R is vinyl, is prepared from the starting material chiral (R)-1,2,4-butane triol and following the same general procedures and reaction sequences as illustrated in reaction scheme 2, for the preparation of the (S)-vinyl isomer.

The racemic mixture (RS) for the compound of Formula I, when R is vinyl can be prepared from the starting material (RS)-1,2,4-butane triol and following the procedures and reactions as illustrated in reaction scheme 2, for the preparation of the (S)-vinyl isomer. The racemic mixture (RS) for the compound of Formula I, when R is vinyl can also be resolved into the (R) and (S) isomer by methods well-known in the art. The (RS)-1,2,4-butane triol is commercially available.

An additional route for the preparation of (S) and (R) chiral isomers of the compound of Formula I, when R is azidomethyl or aminomethyl is illustrated in reaction scheme 3.

Scheme 3

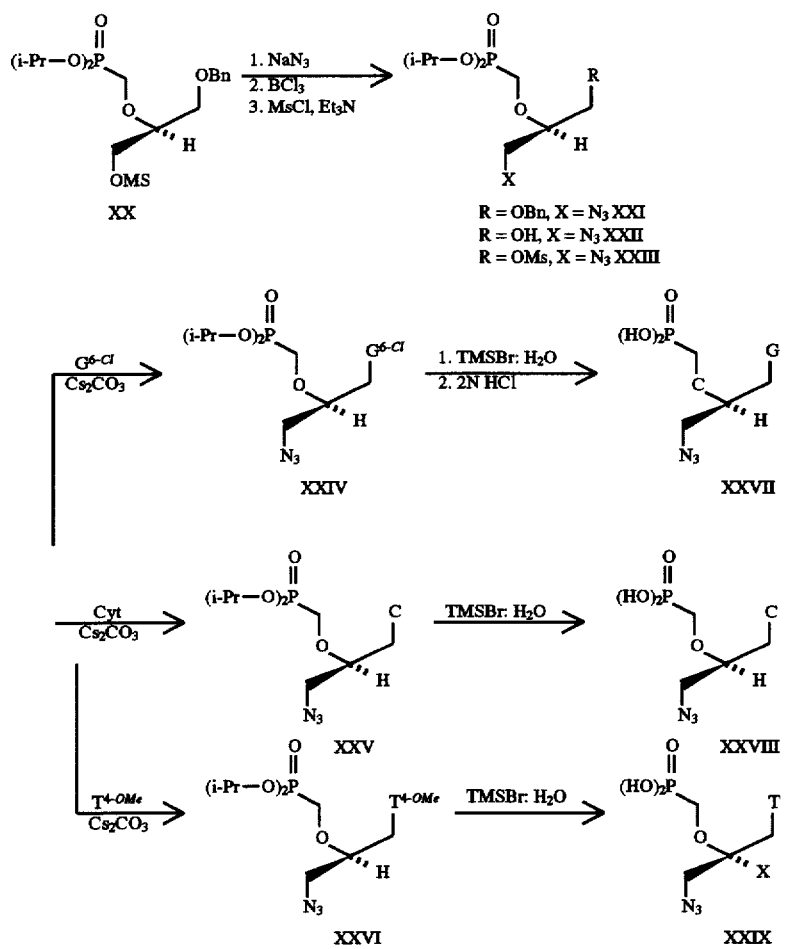

The (R)-3-O-benzyl-2-O-(diisopropylphosphonomethoxy)-1-O-(methanesulfonyl) glycerol of Formula XX, which is prepared by the procedure of J. J. Bronson et al., *J. Med. Chem.*, 32, 1457, 1989, is converted to (R)-3-azido-1-O-benzyl-2-O-(diisopropylphosphonomethoxy)-1,2-propanediol of Formula XXI with sodium azide in an anhydrous organic solvent, for example, N',N'-dimethylformamide. The compound of Formula XXI is converted to (R)-3-azido-2-O-(diisopropylphosphonomethoxy)-1,2-propanediol of Formula XXII with boron trichloride in an inert organic solvent, for example, methylene chloride. The compound of Formula XXII is then converted to (R)-3-azido-2-O-(diisopropylphosphonomethoxy) 1-O-methanesulfonyl-1,2-propanediol of Formula XXIII with methanesulfonylchloride in the presence of an organic base, for example, triethylamine in an inert organic solvent, such as methylene chloride. The compound of Formula XXIII is converted to (S)-2-amino-9-[3-azido-2-(diisopropylphosphonomethoxy)propyl]-6-chloro-purine of Formula XXIV by condensing it with 2-amino-6-chloropurine in the presence of cesium carbonate and N',N'-dimethlformamide. The condensation of the compound of Formula XXIII with cytosine or 4-O-methylthymine in the presence of cesium carbonate and N',N'-dimethylformamide gives the compound (S)-[3-azido-2-[(diisopropylphosphonomethoxy)propyl)cytosine of Formula XXV or the compound (S)-[3-azido-2-[(diisopropylphosphonomethoxy)propyl]-4-O-methylthymine of Formula XXVI, respectively. The compounds of Formulae XXIV or XXV or XXVI are then treated with bromotrimethylsilane, followed by acidic or water hydrolysis to give the compounds (S)-9-[3-azido-2-(phosphonomethoxy)propyl]guanine of Formula XXVII or (S)-9-[3-azido-2-phosphonomethoxy)propyl]cytosine of Formula XXVIII or (S)-9-[3-azido-2-phosphonomethoxy)propyl]thymine of Formula XXIX.

The (R) chiral isomer of the compounds of Formulae XXVII or XXVIII is prepared from the starting material (S)-3-O-benzyl-2-O-(diisopropylphosphonomethoxy)-1-O-(methanesulfonyl)glycerol and following the same reaction sequences as illustrated in the reaction scheme 3. The (R) chiral isomer of the compound of Formula XXIX can be prepared starting with (S)-3-O-benzyl-2-O-(diisopropylphosphonomethoxy)-1-O-(methanesulfonyl)glycerol and following the reaction sequences of scheme 3.

The (S) or (R) isomer of the aminomethyl compounds of Formulae XXVII or XXVIII or XXIX can be prepared by reduction of the corresponding (S) or (R) azidomethyl compounds of Formulae XXVII or XXVIII or XXIX.

Pharmaceutically acceptable salts of Formula I are prepared by methods known in the art. The salts include ammonium salts and salts of physiologically acceptable metals, particularly Li$^+$, K$^+$, Na$^+$, Ca$^{++}$ and Mg$^{++}$, and comprise a further aspect of the invention. Metal salts can be prepared by reacting the metal hydroxide with the Formula I compound of this invention. Examples of metal salts which can be prepared in this way are salts containing Li$^+$, Na$^+$ and K$^+$. A less soluble metal salt can be precipitated from the solution of a more soluble salt by the addition of the suitable metal compound. Acid salts may be prepared by reacting a Formula I compound with an inorganic or organic acid, e.g., HCl, HBr, H$_2$SO$_4$, organic sulfonic acids and the like.

The solvates and hydrates of the compound of Formula I can be prepared by cyrstallizing a compound of Formula I from solvents such as water, methanol, ethanol, etc.

ABBREVIATIONS OF COMPOUNDS

The abbreviations used to identify the compounds of this nucleotide clsss are well-known in the art and are used herein as defined below:

PMEG: 9-[2-(phosphonomethoxy)ethyl]guanine (compound of Example 7 in European Patent Application EP-269,947 and compound 5 in Table 2 of European Patent Application EP-253,412)

(S)-2'-vinyl-PMEG: (S)-9-[2-(phosphonomethoxy)-3-butenyl]guanine (compound of Example 1)

(R)-2'-vinyl-PMEG: (R)-9-[2-(phosphonomethoxy)-3-butenyl]guanine (compound of Example 2)

Racemic-2'-vinyl-PMEG: (RS)-9-[2-(phosphonomethoxy)-3-butenyl]guanine (S)-2'-azidomethyl-PMEG: (S)-9-[3-azido-2-(phosphonomethoxy)propyl]guanine (compound of Example 4)

(R)-2'-azidomethyl-PMEG: (R)-9-[3-azido-2-(phosphonomethoxy)propyl]guanine (compound of Example 5)

Racemic-2'-azidomethyl-PMEG: (RS)-9-[3-azido-2-(phosphonomethoxy)propyl]guanine (S)-2'-azidoethyl-PMEG: (S)-9-[4-azido-2-(phosphonomethoxy)butyl]guanine (compound of Example 11)

(S)-2'-azidoethyl-PMEC: (S)-9-[4-azido-2-(phosphonomethoxy)butyl]cytosine (compound of Example 12)

(S)-2'-azidomethyl-PMEC: (S)-9-[3-azido-2-(phosphonomethoxy)propyl]cytosine (compound of Example 6)

(S)-2'-vinyl-PMEC (S)-9-[2-(phosphonomethoxy)-3-butenyl]cytosine (compound of Example 3)

(S)-2'-azidomethyl-PMET: (S)-9-[3-azido-2-(phosphonomethoxy)propyl]thymine (compound of Example 8)

BIOLOGICAL ACTIVITY

To illustrate the antiviral activity against human immunodeficiency virus (HIV), the compounds of the instant invention and a known compound PMEG are presented in Table I and FIGS. 1–7, along with their relative cytotoxicities.

ASSAYS WITH HUMAN IMMUNODEFICIENCY VIRUS (HIV)

Compounds were evaluated for activity against human immunodeficiency virus (HIV RF strain obtained from Luc Montagnier, Institut Pasteur, Paris, France) in CEM-SS cells (P. L. Nara, et al., in *AIDS Res. Human. Retroviruses*, 1987, 3, 283–302) using the XTT assay described by O. S. Weislow, et al., in *J. Natl. Cancer Instit.*, 1989, 81, 577–586. CEM-SS cells were obtained from Owen Weislow at the National Cancer Institute. Cells were exposed to HIV and cultured in microtiter plates in the presence of test compounds at concentrations of 0.32, 1, 3.16, 10, 31.6, 100, 316 and 1000 um. On day six post-infection, the antiviral effect was measured using the XTT assay in which an optical density (OD) reading is obtained at each drug concentration. The optical density reading is proportional to the number of viable cells. Plots of drug concentration versus relative optical density readings are shown in FIGS. 1–7. The relative optical density values were derived by dividing the sample observed optical density by the value obtained for the control. Assays run in infected cells show the antiviral effect of the test compounds, where an increase in the number of viable cells (higher OD reading) reflects the protective, antiviral activity of the compound. Assays run in uninfected cells provide a measure of cellular toxicity.

The antiviral effect is also expressed (see Table 1) as the concentration of compound which increases the number of viable cells in infected cultures to 50%, to that of the untreated, uninfected control cultures (ED$_{50}$). The cellular toxicity is expressed as the concentration of compound which reduces the number of viable cells to 50%, to that of the untreated control (TD50). The selectivity index (SI) is the ratio of TD$_{50}$ to ED$_{50}$.

The anti-HIV activity and cellular toxicity of the test compounds are plotted in FIGS. 1–7 as a function of relative optical density versus increasing log concentrations of the test compounds (XTT assay). FIGS. 1–7 visually show the results of the relative anti-HIV activity of the test compounds on infected cells (—●—) and the cellular toxicity of the same test compound on uninfected cells (—■—).

Figure 2:
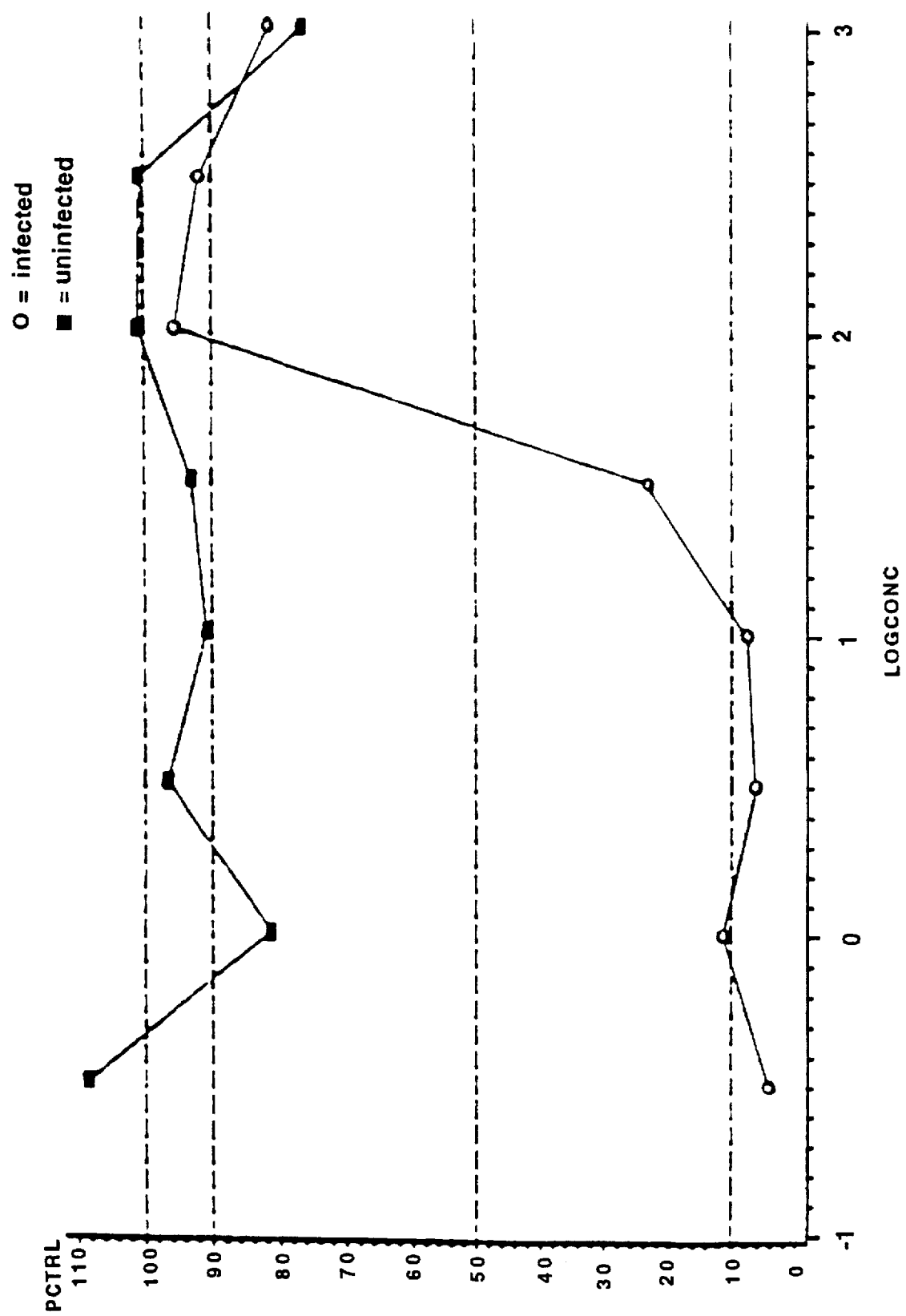
Figure 3:
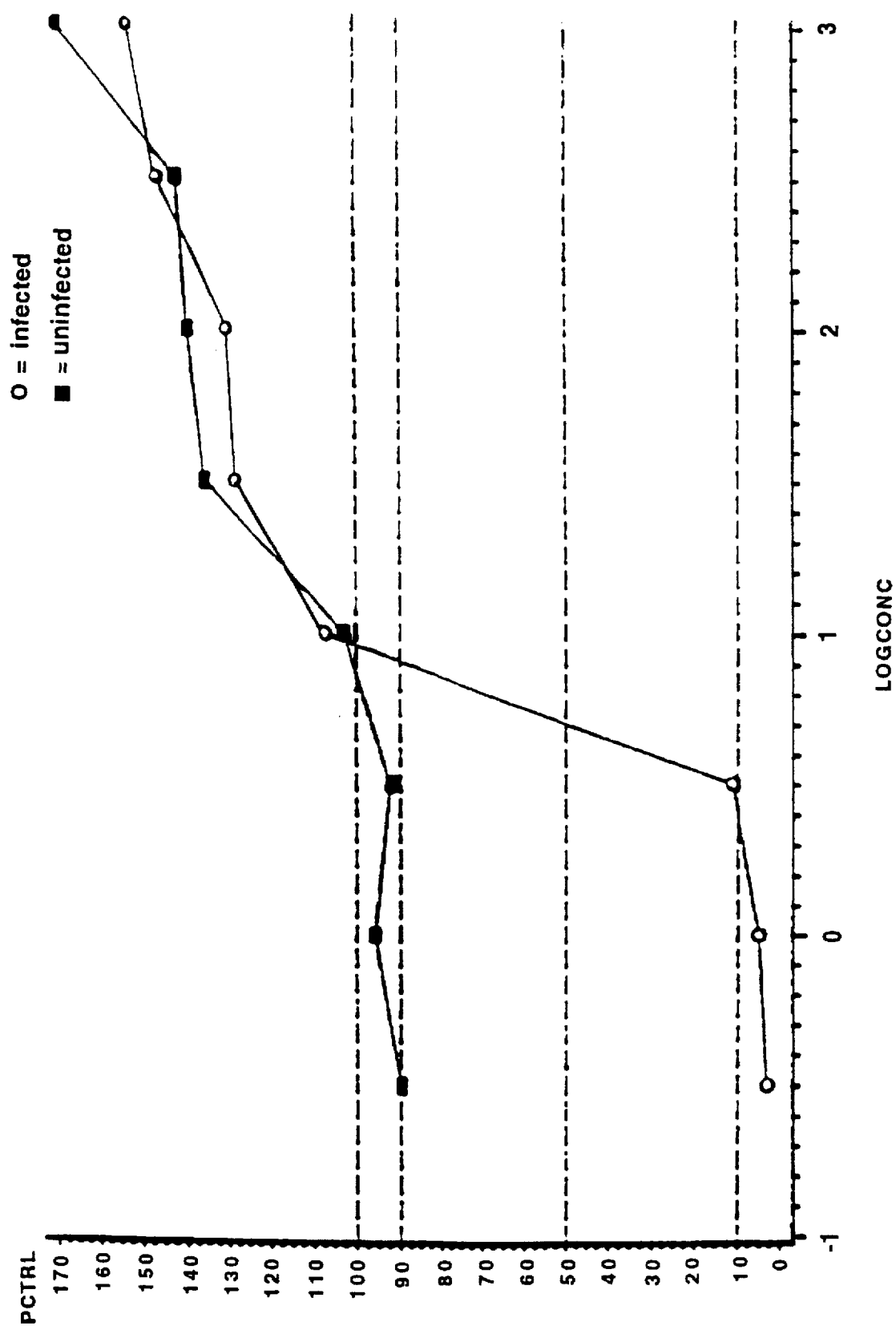
Figure 4:
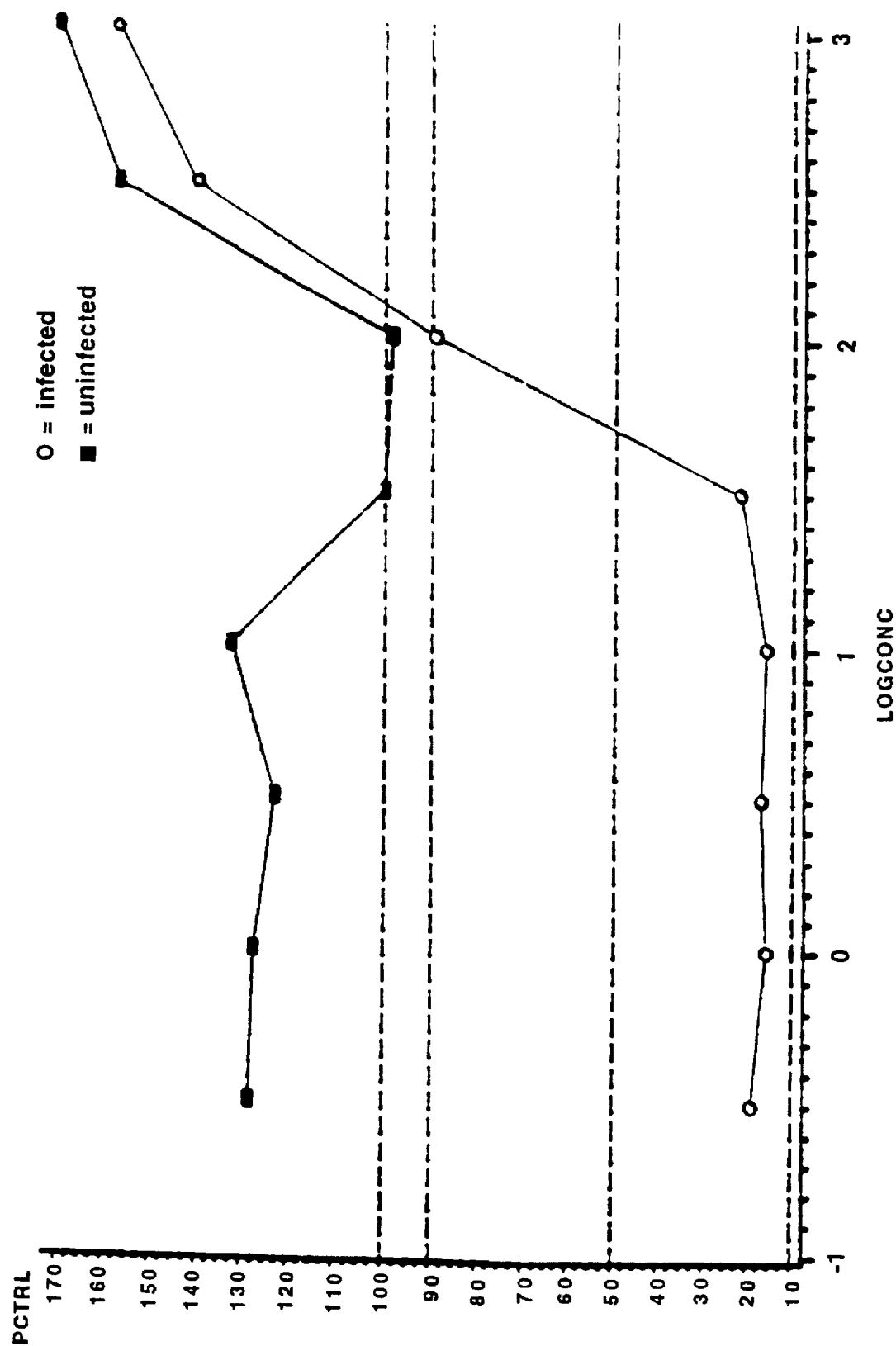
Figure 5:
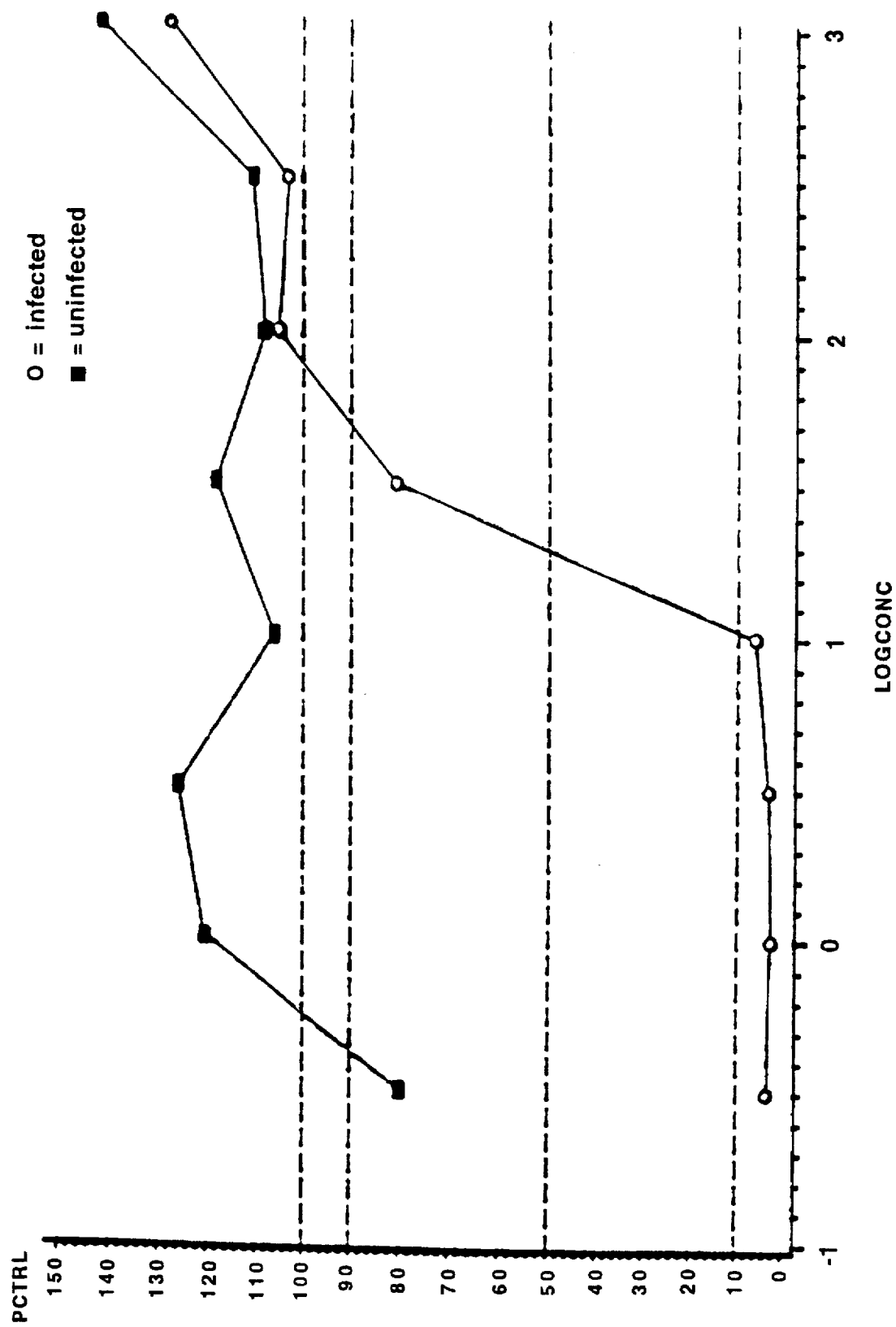
Figure 6:
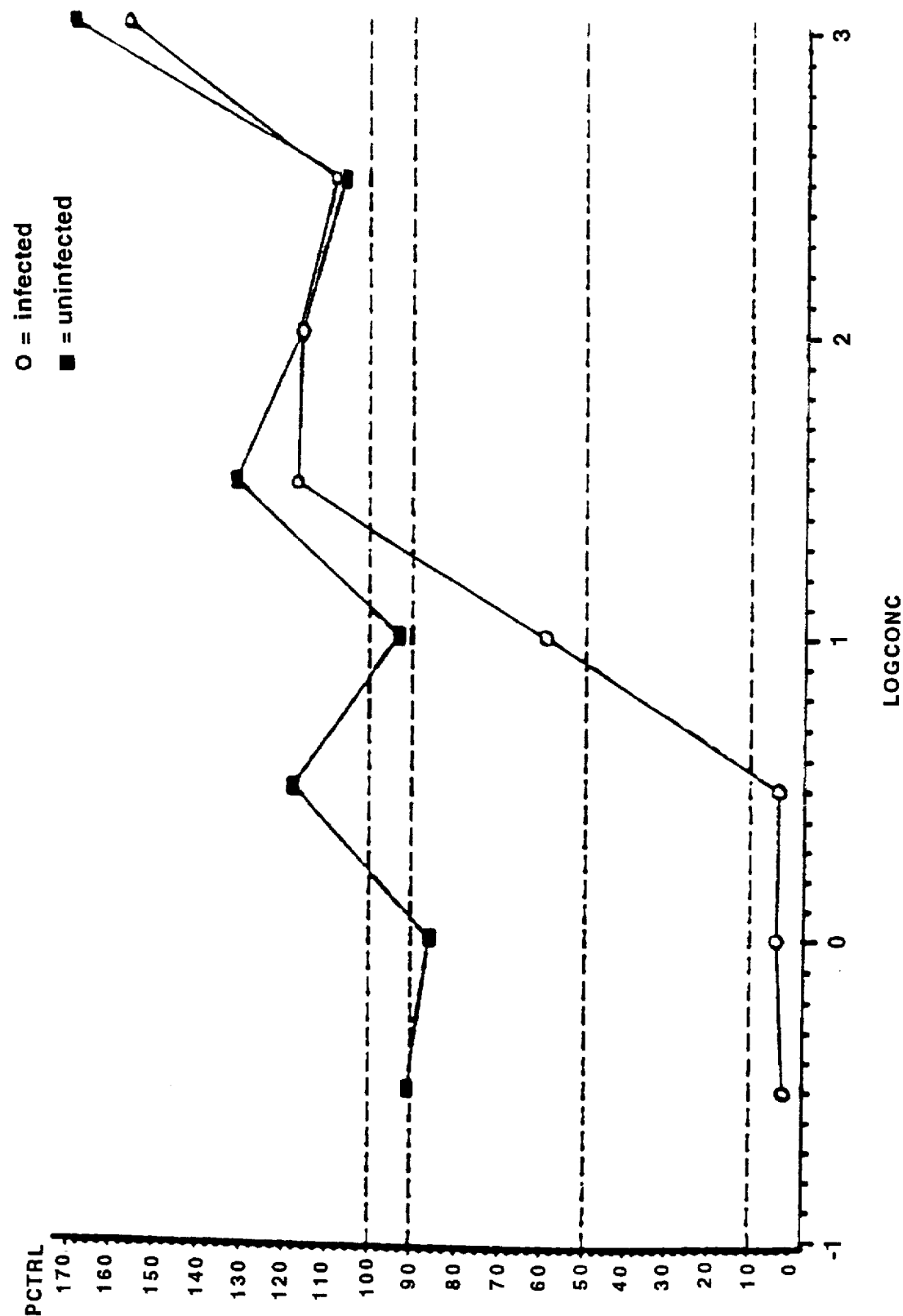
Figure 7:
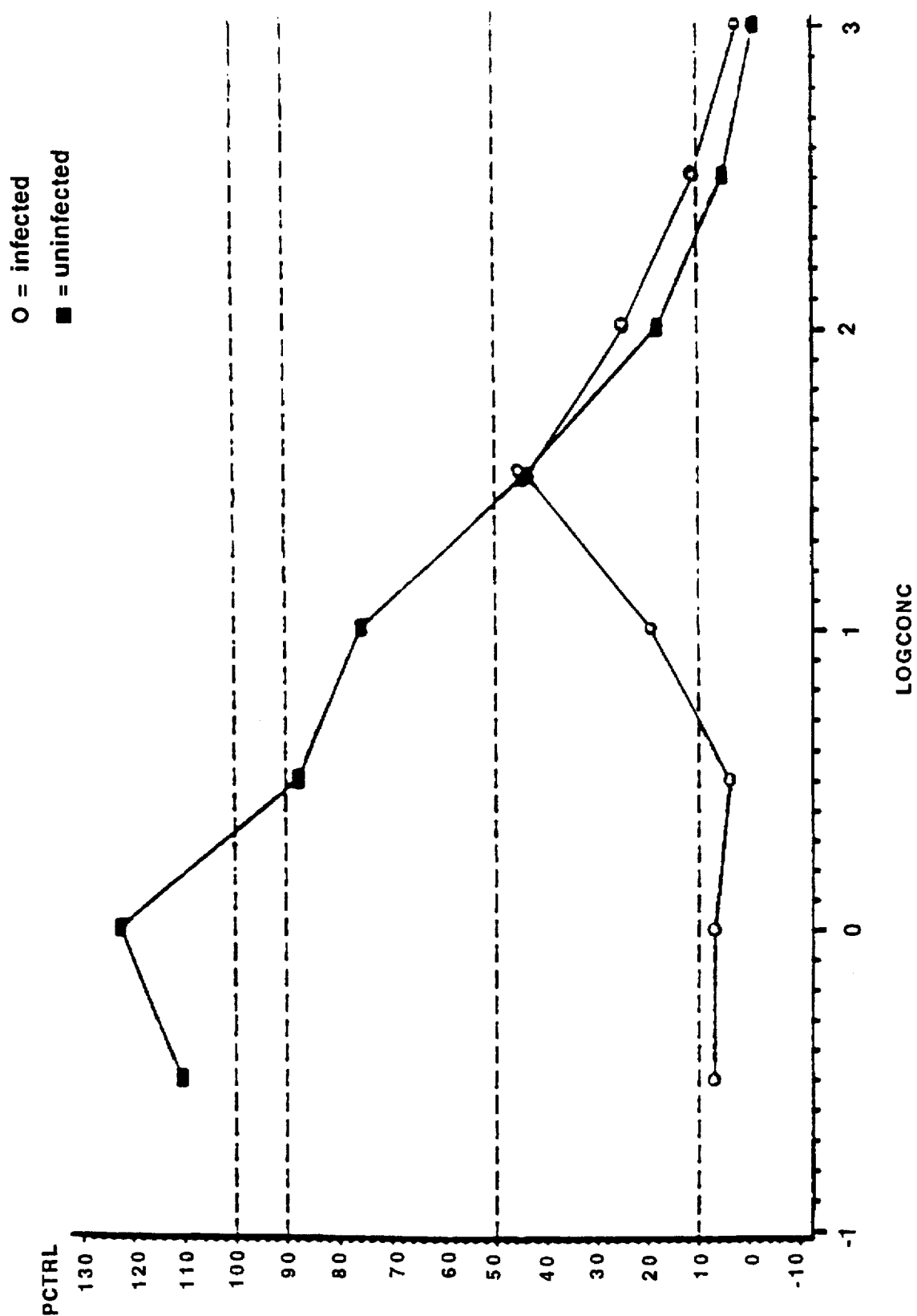

The anti-HIV activity of the (R)-2'-vinyl- PMEG of the instant invention is shown in FIG. 1 (CEM-SS cells) while the (S)-2'-vinyl-PMEG is shown in FIG. 2 (CEM-SS cells). The anti-HIV activity of the comparison compound PMEG is shown in FIG. 7 (CEM-SS cells). The anti-HIV activity of (R)-2'-azidomethyl-PMEG and (S)-2'-azidomethyl-PMEG is shown in FIGS. 3 and 4. The anti-HIV activity of the racemic (RS)-2'-vinyl PMEG and (RS)-2'-azidomethyl-PMEG is shown in FIGS. 5 and 6. FIG. 1 shows that, over a concentration range of 5 to 100 µM, (R)-2'-vinyl-PMEG provides complete protection from the human immunodeficiency virus in CEM-SS cell lines with no observed cellular toxicity at concentrations less than 100 µM. FIG. 2 shows that (S)-2'-vinyl-PMEG provides complete protection from HIV in CEM-SS cells at 100 µM with no observed cellular toxicity at concentrations less than 100 µM. By comparison, as shown in FIG. 7 PMEG does exhibit some anti-HIV effect in CEM-SS cells, but the cellular toxicity of PMEG prevents protection from the virus.

Selectivity Index of Test Compounds

Another estimate of the effectiveness of a compound for use against HIV in the prevention and/or treatment of AIDS is a selectivity index (an in vitro "therapeutic index"), the ratio of the toxic dose 50 to the effective dose 50. The selectivity index (SI) for (RS), (R)- and (S)-2'-vinyl-PMEG and (RS), (R), (S), -2'-azidomethyl-PMEG of the instant invention and for the comparison compound PMEG are shown in Table 1. The data in Table 1 clearly shows that (R)-2'-vinyl-PMEG and (R)-2'-azidomethyl-PMEG are both potent and selective anti-HIV agents as compared to the other compounds.

TABLE 1

Anti-HIV RF Activity in CEM-Cells Evaluated by XTT Assay Six Days Post Infection

| Compound | $ED_{50}$ (μM)[a] | $TD_{50}$ (μM)[b] | SI[c] |
|---|---|---|---|
| PMEG | 0.2 | 15 | 30 |
| (R)-2'-vinyl-PMEG | 12.6 | >1000 | >79 |
| (R)-2'-vinyl-PMEG | 48.5 | >1000 | >21 |
| (R,S)-2'vinyl-PMEG[d] | 19.6 | >1000 | >51 |
| (R)-2'-azidomethyl-PMEG | 5.0 | >1000 | >200 |
| (S)-2'-azidomethyl-PMEG | 51.0 | >1000 | >20 |
| (R,S)-2'-azidomethyl-PMEG[d] | 8.0 | >1000 | >125 |
| (S)-2'-azidoethyl-PMEG[e] | >500 | >500 | NA[f] |
| (S)-2'-azidoethyl-PMEC[e] | >500 | >500 | NA[f] |
| (S)-2'-azidomethyl-PMEC[e] | >500 | >500 | NA[f] |
| (S)-2'-vinyl-PMEC[e] | >500 | >500 | NA[f] |
| (S)-2'-azidomethyl-PMET[g] | >500 | >500 | NA[f] |

[a]Effective Dose 50: In infected cells, concentration of compound which results in an increase in the number of viable cells to 50% to that of uninfected control.
[b]Toxic Dose 50: In uninfected cells, concentration of compound which results in a 50% decrease of viable cells.
[c]Selectivity Index: Ratio of $TD_{50}$ to $ED_{50}$.
[d]The sample was prepared by mixing the (R) and (S) isomers in a 1 to 1 ratio.
[e]The compounds were evaluated using human immunodeficiency virus LAV BRU strain obtained from Luc Montagnier, Institut Pasteur, Paris, France.
[f]NA: not available.
[g]The compound was evaluated by Southern Research Institute using human immunodeficiency virus HTLV-IIIB strain and MT-2 cells (S. Harada, et. al., Science, 1985, 229, 563).

The cytotoxicity of PMEG, (R)2'-vinyl-PMEG, (S)-2'-vinyl-PMEG and (R)-2'-azidomethyl-PMEG was also determined by the cell growth inhibition assay in CEM-SS cells. The CC50 values of these four compounds are listed in Table 2.

TABLE 2

Cell Growth Inhibition Assay in CEM-SS Cells

| Compound | CC50 (μM)* |
|---|---|
| PMEG | 2.4 |
| (R)-2'-vinyl-PMEG | 1600 |
| (S)-2'-vinyl-PMEG | 1600 |
| (R)-2'-azidomethyl-PMEG | 1400 |

*CC50 is the concentration of drug that causes a 50 percent decrease in cell count as compared to the control at day three (72 hours).

The above values show that the (R)-2'-vinyl-PMEG, (S)-2'-vinyl-PMEG and (R)-2'-azidomethyl-PMEG are relatively non-toxic in CEM-SS cells when compared to PMEG.

Protocol for the above assay is given below:
1. Choose proper range of the concentrations of the drug to be evaluated.
2. Prepare the stock solutions of drugs in RPMI 1640 medium at 10× of the highest concentration needed in cell culture
3. Make serial dilution of the 10× stock solutions with RPMI 1640 as needed, usually four different concentrations are used for each drug.
4. Prepare CEM cell suspension at @5×10⁴ cells/ml concentration
5. To each 18 ml CEM cell suspension add 2 ml of properly diluted drug solution (from step 2 and 3) separately and mix well.
6. For cell control, 2 ml of RPMI 1640 is added in place of the drug solutions.
7. Two ml of the solutions from step 5 and 6 are dispensed in to the wells of 24-well plate as shown in the following diagram

```
Time
drug conc.*    24 hr  48 hr  72 hr  96 hr
500 μg/ml      [X]    [ ]    [ ]    [X]
100 μg/ml      [X]    [ ]    [ ]    [X]
 20 μg/ml      [X]    [ ]    [ ]    [X]
  4 μg/ml      [X]    [ ]    [ ]    [X]
```

*the concentrations used for $N_3$— and vinyl- analogs of PMEG.

8. At time zero, cells in 4 wells from the control (no drug added) are counted
9. At 24, 48, 72 and 96 hr post drug addition, both drug treated and control cells are counted
10. All assay are done in duplicate, two 24-well plates are set up for each drug
11. Cell counts obtained from drug treated cultures are compared to those from control cultures.
12. The concentration of drug that causes a 50 percent of decrease of cell number as compared to the control at day three (72 hr) is assigned as the $CC_{50}$ value of the drug.

The invention, accordingly, provides compounds of Formula I and their pharmaceutically acceptable salts and solvates thereof and, preferably, the compound of Formula I which is (R)-isomer and its pharmaceutically acceptable salts and solvates thereof for use in the therapy or prophylaxis of viral infections, especially human immunodeficiency virus, in a human subject.

The compounds of this invention, including the pharmaceutically acceptable salts and solvates thereof, have desirable antiviral activity. They exhibit activity against retroviruses. In particular, the compound of Formula I exerts a significant anti-HIV effect with no observed cytotoxicity.

For use against viral infections, the compounds of this invention may be formulated into pharmaceutical preparations in any convenient way, and the invention, therefore, also includes, within its scope, pharmaceutical compositions comprising a compound of Formula I or a pharmaceutically acceptable salt or solvate thereof adapted for use in human medicine. Such compositions may be presented for use in conventional manner in admixture with one or more pharmaceutically acceptable carriers or excipients. The reference *Remington's Pharmaceutical Sciences*, 15th Edition, by E. W. Martin (Mark Publishing Company, 1975), discloses typical carriers and methods of preparation.

For antiviral purposes, the compounds may be administered topically or systemically. By systemic administration is intended oral, rectal, and parenteral (i.e., intramuscular, intravenous, subcutaneous, and nasal) routes. Generally, it will be found that, when a compound of the present invention is administered orally, a larger quantity of the active agent is required to produce the same effect as the smaller quantity given parenterally. In accordance with good clinical practice, it is preferred to administer the instant compounds at a concentration level that will produce effective antiviral without causing any harmful or untoward side effects.

Therapeutically and prophylactically the instant compounds are given as pharmaceutical compositions comprised of an effective antiviral amount of a compound of Formula I or a pharmaceutically acceptable salt thereof and a pharmaceutically acceptable carrier, as stated hereinabove. Pharmaceutical compositions for effecting such treatment will contain a major or minor amount, e.g., from 95% to 0.5% of at least one compound of the present invention in combination with a pharmaceutical carrier, the carrier comprising one or more solid, semi-solid, or liquid diluents, fillers, and formulation adjuvants which are non-toxic, inert, and pharmaceutically acceptable. Such pharmaceutical compositions are preferable in dosage unit form; i.e., physically discreet units containing a predetermined amount of the drug corresponding to a fraction or multiple of the dose which is calculated to produce the desired therapeutic response. Other therapeutic agents can also be present. Pharmaceutical compositions providing from about 0.1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g., syrup, acacia, gelatin, sorbitol, tragacanth, or polyvinylpyrrolidone), fillers (e.g., lactose, sugar, maize-starch, calcium phosphate, sorbitol, or glycine), lubricants (e.g., magnesium stearate, talc, polyethylene glycol, or silica), disintegrants (e.g., starch), and wetting agents (e.g., sodium lauryl sulfate). Solutions or suspensions of a Formula I compound with conventional pharmaceutical vehicles are employed for parenteral compositions, such as an aqueous solution for intravenous injection or an oily suspension for intramuscular injection. Such compositions having the desired clarity, stability, and adaptability for parenteral use are obtained by dissolving from 0.1% to 10% by weight of the active compound in water or a vehicle consisting of a polyhydric aliphatic alcohol, such as glycerine, propylene glycol, and polyethylene glycol or mixtures thereof. The polyethylene glycols consist of a mixture of non-volatile, usually liquid, polyethylene glycols which are soluble in both water and organic liquids and have molecular weights from about 200 to 1500.

Considering the biological activities possessed by the compounds of the instant invention, it can be seen that these compounds have antiviral properties particularly suited to their use in combating acquired immunodeficiency syndrome (AIDS). Thus, another aspect of the instant invention concerns a method for treating HIV infections in mammals, including humans, in need of such treatment which comprises systemic or topical administration to such mammal of an effective dose of a Formula I compound or a pharmaceutically acceptable salt or solvate thereof. A further aspect of the instant invention concerns a method for treating human cells infected with HIV infections which comprises systemic or topical administration to such cells of an effective dose of a Formula I compound or a pharmaceutically acceptable salt or solvate thereof. On the basis of testing, an effective dose could be expected to be from about 0.001 to about 30 mg/kg body weight. It is envisioned that, for clinical antiviral application, compounds of the instant invention will be administered in the same manner and use as for the reference drugs AZT, DDI, and D4T. For clinical applications, however, the dosage and dosage regimen must, in each case, be carefully adjusted, utilizing sound professional judgment by the physician and consideration of the age, weight, and condition of the patient, the route of administration, and the nature and gravity of the illness. Generally, a daily oral dose will comprise from about 0.1 to about 750 mg, preferably 10-500 mg of a Formula I compound administered from 1 to 3 times a day. In some instances, a sufficient therapeutic effect can be obtained at lower doses while larger doses will be required in others. It is also envisioned that a compound of Formula I may be administered on a weekly schedule, such as once or twice per week; the dosage to be used in such a regimen may be adjusted with due consideration of factors listed above and to maintain serum drug level at an anti-HIV effective level.

DESCRIPTION OF SPECIFIC EMBODIMENTS

In the following examples, all temperatures are given in degrees Centigrade. Melting points were recorded on an Electrothermal digital capillary melting point apparatus, and temperatures are uncorrected. Proton magnetic resonance ($^1$H NMR) spectra were recorded on a Bruker AM 300, or Varian Gemini 300 spectrometer. All spectra were determined in $CDCl_3$, $DMSO-d_6$, or $D_2O$ unless otherwise indicated, and chemical shifts are reported in units downfield from the internal standard tetramethylsilane (TMS), and interproton coupling constants are reported in Hertz (Hz). Splitting patterns are designated as follows: s, singlet; d, doublet, t, triplet; q, quartet; m, multiplet; br, broad peak; and dd, doublet of doublet. Carbon-13 nuclear magnetic resonance ($^{13}$C NMR) spectra were recorded on a Bruker AM 300 or Varian Gemini 300 spectrometer and were broad band proton decoupled. All spectra were determined in $CDCl_3$, $DMSO-d_6$, or $D_2O$ unless otherwise indicated with internal deuterium lock, and chemical shifts are reported in units downfield from tetramethylsilane, relative to an internal standard. Infrared (IR) spectra were determined on a Perkin-Elmer 1800 FT-IR spectrometer from 4000 $cm^{-1}$ to 400 $cm^{-1}$, calibrated to 1601 $cm^{-1}$ absorption of a polystyrene film, and are reported in reciprocal centimeters ($cm^{-1}$). Optical rotations $[\alpha]^{20}$ were determined on a Perkin-Elmer 41 polarimeter in the solvents indicated. Mass spectra were recorded on a Kratos MS-50 or a Finnegan 4500 instrument utilizing the fast atom bombardment (FAB) or direct chemical ionization (DCI) technique. The mass data are expressed in the format: protonated parent ion ($MH^+$).

Column chromatography, also referred to as flash column chromatography, was performed in a glass column using finely divided silica gel (32–63 m on silica gel-H) and pressures somewhat above atmospheric pressure with the indicated solvents. UV was determined on Hewlett Packard 8452A Diode Array Spectrometer. The solvent in which the UV was determined are indicated in the experiment section.

All evaporations of solvents were performed under reduced pressure. Celite is a registered trademark of the Johns-Manville Products Corporation for diatomaceous earth. As used herein, the term hexanes is a mixture of isomeric $C_6$ hydrocarbons as specified by the American Chemical Society, and the term "inert" atmosphere is an argon or nitrogen atmosphere unless otherwise indicated.

EXAMPLE 1

(S)-9-[2-(phosphonomethoxy)-3-butenyl]guanine ((S)-2'-vinyl PMEG)

(S)-2,2-Diisopropyl-4-(2-hydroxyethyl)dioxolane

To a 1-l three-neck flask equipped with a mechanic stirrer, Dean-Stark trap and condenser, (S)-1,2,4-butane triol (48 g, 0.45 mol), 2,4-dimethyl-3-petanone (180 ml, 1.27 mol) and p-luenesulfonatic acid (0.35 g) were mixed in 300 mL of bezene. After the mixture was gently reflux for 20 h, the mixture was cooled to room temperature and 10 mL of triethylamine was added. The solvent was evaporated. The residue was purified by flash chromatography on silica gel (acetone:methylene chloride=1:10 to 1:2) to give 77.2 g (84% yield) of the product as an oil.

$[\alpha]^{20}_D$ +1.6° (c 15.6 $CH_2Cl_2$).

$^1$H NMR (300 MHz, $CDCl_3$) δ 4.33–4.23 (m, 1H, H-4), 4.14 (t, J=7.0 Hz, H-5), 3.85–3.72 (m, 2H, H-2'), 3.49 (t,

J=8.3 Hz, 1H, H-5), 2.10–1.97 (m, 2H, C$\underline{H}$CH$_3$), 1.90–1.65 (m, 2H, H-1'), 0.90–0.86 (m, 12H, C$\underline{H}_3$).

$^{13}$C NMR (75 MHz, CDCl$_3$) δ 116.7 (C—O—C), 77.2 (C-4), 72.2 (C-5), 60.9 (C-2'), 35.0 (C-1'), 34.3, 33.5 (C$\underline{H}$CH$_3$), 14.3, 17.2, 17.0 (CH$\underline{C}$H$_3$).

MS (isobutane, DCI): m/e=203 (MH$^+$).

Anal. Calcd for C$_{11}$H$_{22}$O$_3$: C, 65.31; H, 10.96. Found: C, 65.25; H, 11.11.

(S)-4-O-Benzyl-1,2,4-butanetriol (S)-2,2-Diisopropyl-4-(2-hydroxyethyl)dioxolane (76.2 g, 0.377 mol), benzylbromide (129 g, 0.753 mol) and tetrabutylammonium iodide (7 g, 19 mmol) were mixed with a concentrated sodium hydroxide solution (40 g in 90 mL of water, 2.26 mol) in a 3-neck flask equipped with a mechanic stirrer and a condenser. After stirred at 110° C. for 18 hours, the mixture was cooled to room temperature and the organic layer was separated. The aqueous layer was extracted with methylene chloride (100 mL×2). The combined methylene chloride extrats were dried over magnesium sulfate. The solvent was evaporated, and the residue was treated with 300 mL of 1.5M sulfuric acid. After stirred at 100° C. for 8 hours, the mixture was cooled to room temperature, and hexane (300 mL) was added. The aqueous layer was washed with hexane twice (200 mL×2), and then ajusted pH to 8–9 with concentrated sodium sodium hydroxide. The solution was extrated with ethyl acetate (200 mL×3). The combined ethyl acetate extrates were dried over magnesium sulfate. The solvent was evaporated, and the residue was purified by fractional distillation in vacuo (0.1 mmHg, bp 150°–170° C.) to give 68.3 g (92% yield) of the title compound as an oil.

$^1$H NMR (300 MHz, CDCl$_3$) δ 7.48–7.24 (m, 5H, Ph), 4.51 (s, 2H, C$\underline{H}_2$Ph), 3.96–3.84 (d, 1H, H-2), 3.74–3.53, 3.53–3.42 (m, 4H, H-1 and H-4), 2.24 (bs, 1H, OH), 3.08 (bs, 1H, OH), 1.88–1.58 (m, 2H, H-3).

$^{13}$C NMR (75 MHz, CDCl$_3$) δ 137.9, 128.6, 128.0, 127.9 (Ph), 73.3 (C$\underline{H}_2$Ph), 71.2 (C-2), 68.1 (C-4), 66.5 (C-1), 32.6 (C-3).

MS (isobutane, DCI): m/e=196 (MH$^+$)

(S)-4-O-Benzyl-1-O-[(p-methoxyphenyl)diphenylmethyl]-1,2,4-butanetriol (S)-4-O-Benzyl-1,2,4-butanetriol (68.3 g, 348 mmol) was mixed with triethylamine (70.4 g, 696 mmol) and dimethylaminopyridine (3.42 g, 28 mmol) were mixed in methylene chloride (300 mL) under nitrogen atmosphere. To the solution p-anisylchlorodiphenylmethane (129.1 g, 418 mmol) was added at 0° C. The reaction mixture was stirred at 0° C. for 30 min and then at room temperature for 5 hours. Saturated sodium bicarbonate was added to the mixture and the resulting mixture was stirred at room temperature for 1 hour. The aqueous layer was extracted with methylene chloride (150 mL×2). The combined methylene chloride extracts were dried over mganesium sulfate. The solvent was evaporated, and the residue was purified by flash chromatography on silica gel (ethyl acetate:hexane=1:5 to 1:1) to give 155.5 g (95% yield) of the title compound as a thick oil.

[α]$^{20}_D$ −3.0° (c 3.29 MeOH)

$^1$H NMR (300 MHz, CDCl$_3$) δ 7.43–7.40, 7.32–7.15, 6.82–6.79 (m, 14H, Ar), 4.44 (s, 2H, C$\underline{H}_2$Ph), 4.03–3.93 (m, 1H, H-2), 3.76 (s, 3H, OC$\underline{H}_3$), 3.64–3.50 (m, 2H, H-4), 3.12–3.05 (m, 2H, H-1), 2.80 (d, J=2.0 Hz, 1H, OH), 1.80–1.70 (m, 2H, H-3).

$^{13}$C NMR (300 MHz, CDCl$_3$) δ 158.7, 144.6, 138.2, 135.7, 130.5, 128.5, 127.9, 127.7, 127.0, 113.1, 88.2, 73.1 (C$\underline{H}_2$Ph), 67.9, 67.2 (C-4 and C-1), 65.0 (OC$\underline{H}_3$), 33.2 (C-3).

Anal. Calcd for C$_{31}$H$_{32}$O$_4$: C, 79.45; H, 6.88. Found: C, 79.21; H, 7.05.

(S)-4-O-Benzyl-O-2-[(diisopropyl phosphonomethyl)]-1,2,4-butanetriol

To a solution of (S)-4-O-Benzyl-1-O-[(p-methoxyphenyl)diphenylmethyl]-1,2,4-butanetriol (153.5 g, 327.6 mmol) in dry tetrahydrofuan (700 mL), sodium hydride (80% in mineral oil, 11.8 g, 393 mmol) was added portionwise under nitrogen atmosphere. After heated at reflux for 5 hours, the mixture was cooled in an ice bath. Tosyloxymethyl diisopropylphosphonate (137.7 g, 393.1 mmol) in 300 mL of dry tetrahydrofuran was slowly added to the mixture. The mxture was stirred at 0° C. for 30 min and at room temperature for 14 hours. The resulting slurry was filtered through a pad of celite. The filtrate was evaporated, and methylene chloride (400 mL) and water (200 mL) were added to the residue. The aqueous layer was extrated with methylene chloride (200 mL×2). The combined extracts were dried over magnesium sulfate. The solvent was evaporated, and methanol (400 mL) and toluenesulfonic acid (10 g) were added. The mixture was stirred at about 60° C. for 8 hour. The solvent was evaporated, and the residue was purified by flash chromatography on silica gel (ethyl acetate:hexane=1:3 to 1:0, then ethyl acetate:ethanol=10:1) to provide 44.1 g (37% yield) of the title compound as an oil.

$^1$H NMR (300 MHz, CDCl$_3$) δ 7.38–7.24 (m, 5H, Ar), 4.80–4.63 (m, 2H, POC$\underline{H}$), 4.49 (d, J=12.0 Hz, 1H, C$\underline{H}_2$Ph), 4.44 (d, J=12.0 Hz, 1H, C$\underline{H}_2$Ph), 3.87 (dd, J=7.2, 14.1 Hz, 1H, C$\underline{H}_2$P), 3.72 and 3.80–3.60 (dd over m, J=9.0, 14.1 Hz, 2H, C$\underline{H}_2$P and H-2), 3.60–3.47 (m, 4H, H-1 and H-4), 1.82–1.70 (m, 2H, H-3), 1.36–1.25 (m, 12H, POCH CH$_3$).

$^{13}$C NMR (75 MHz, CDCl$_3$) δ 138.8, 129.0, 128.3 (Ph), 82.1 (d, $^3$J$_{c,p}$=8.7 Hz, C-2), 73.4 (C$\underline{H}_2$Ph), 72.0 (d, $^2$Jc,p=7 Hz, PO$\underline{C}$H), 71.6 (d, $^2$Jc,p=7 Hz, PO$\underline{C}$H), 66.7 (C-4), 65.4 (d, $^1$Jc,p=170 Hz, $\underline{C}$H$_2$P), 64.9 (C-1), 31.8 (C-3), 24.2 (m, POCH$\underline{C}$H$_3$).

(S)-4-O-Benzyl-2-O-(Diisopropylphosphonomethyl)-1-O-methoxymethyl-1,2,4-butanetriol To a solution of (S)-4-O-Benzyl-O-2-[diisopropyl(phosphonomethyl)]-1,2,4-butanetriol (20 g, 53.42 mmol) and diisopropylethylamine (13.8 g, 106.8 mmol) in 100 mL of methylene chloride, chloromethyl methyl ether (6.45 g, 80.13 mmol) was added at 0° C. under nitrogen atmosphere. The resulting solution was stirred at room temperature for 14 hours. Methylene chloride (100 mL) and 1N hydrochloric acid (100 mL) were added. The aqueous layer was extracted with methylene chloride (75 mL×2). The combined extracts were washed with saturated sodium bicarbonate solution (100 mL) and brine (100 mL), dried over magnisium sulfate. The solvent was evaporated, the residue was purified by flash chromatography on silica gel (ethyl acetate:petroleum ether=1:1 to 1:0) to give 21.9 g (98% yield) of the product as an oil.

$^1$H NMR (300 MHz, CDCl$_3$) δ 7.33–7.20 (m, 5H, Ar $\underline{H}$), 4.76–4.62 (m, 2H, POC$\underline{H}$), 4.58 (s, 2H, OC$\underline{H}_2$Ph), 4.47 (s, 2H, OC$\underline{H}_2$O), 3.94 (dd, J=8.7, 13.6 Hz, 1H, C$\underline{H}_2$P), 3.74 and 3.75–3.69 (dd over m, J=9.5, 13.6 Hz, 2H, C$\underline{H}_2$P and H-2), 3.65–3.50 (m, 4H, H-1 and H-4), 1.80 (q, J=6.2 Hz, 2H,H-3), 1.32–1.26 (m, 12H, POCHC$\underline{H}_3$).

$^{13}$C NMR (75 MHz, CDCl$_3$) δ 138.4, 128.3, 127.6, 96.4 (O$\underline{C}$H$_2$O), 77.9 (d, $^3$Jc,p=13 Hz, C-2), 72.7 ($\underline{C}$H$_2$Ph), 70.6

(d, $^2$Jc,p=6 Hz, POCH), 69.6 (C-1), 66.2 (C-4), 64.7 (d, $^1$Jc,p=170 Hz, CH$_2$P), 54.9 (OCH$_3$), 31.5 (C-3), 23.6 (t, $^3$Jc,p=6 Hz, POCHCH$_3$).

MS (DCI, isobutene): m/e=419 (MH$^+$).

(S)-2-O-(Diisopropylphosphonomethyl)-1-O-methoxymethyl-1,2,4-butanetriol

Palladium hydroxide on carbon (20%, 10 g) was added to a solution of 4-O-benzyl-2-O-(diisopropylphosphonomethyl)-1-O-methoxymethyl-1,2,4-butanetriol (21.9 g, 52.33 mmol) in a mixture of ethanol and cyclohexene (200 mL of each). The resulting mixture was heated at reflux for 6 hours. The mixture was cooled to room temperature and filtered. The filtrate was evaporated and the residue was purified by flash chromatography on silica gel (methylene chloride:methanol=20:1 to 10:1) to give 16.79 g (98% yield) of the title compound as an oil.

$[\alpha]^{20}_D$ +3.4° (c 2.33, MeOH).

$^1$H NMR (300 MHz, CDCl$_3$) δ 4.80–4.60 (m, 2H, 2×POCH), 4.60 (s, 2H, OCH$_2$O), 4.03–3.80 and 3.67–3.48 (m, 7H, H-1, H-2, H-4, and CH$_2$P), 1.80–1.50 (m, 2H, H-3), 1.34–1.29 (m, 12H, POCHCH$_3$).

$^{13}$C NMR (75 MHz, CDCl$_3$) δ 96.5 (OCH$_2$O), 77.7 (d, $^3$Jc,p=14 Hz, C-2), 71.1 (d, $^2$Jc,p=7 Hz, POCH), 70.2 (C-1), 64.7 (d, $^1$Jc,p=167 Hz, CH$_2$P), 57.9 (C-4), 55.0 (OCH$_3$), 34.3 (C-3), 23.6 (t, $^3$Jc,p=5 Hz, POCHCH$_3$).

MS (isobutane, DCI): m/e=329 (MH$^+$).

Anal. Calcd for C$_{13}$H$_{29}$O$_7$P: C, 47.55; H, 8.90. Found: C, 47.50; H, 8.93.

(S)-2-O-(Diisopropyl phosphonomethyl)-1-O-methoxymethyl-3-butene-1,2-diol

To a solution of (S)-2-O-(diisopropyl phosphonomethyl)-1-methoxymethyl-1,2,4-butanetriol (9.0 g, 27.41 mmol) and 2-nitrophenyl selenocyanide (9.33 g, 41.12 mmol) in anhydrous tetrahydrofuran (100 mL), tributylphosphine (10.3 g, 41.12 mmol) was slowly added at 0° C. under nitrogen. The mixture was stirred at 0° C. for 30 min, and at room temperature for 1 day. Water (100 mL) was added and the aqueous layer was separated, and extrated with ethyl acetate (150 mL×2). The combined organic extracts were dried over magnesium sulfate. The solvent was evaporated, and the residue was purified by flash chromatography on silica gel (ethyl acetate:hexane=1:1 to 1:0 and then ethyl acetate:acetone 10:1) to give (S)-2-O-diisopropyl phososphonomethyl)-1-O-methoxymethyl-4-(2-nitrophenyl)selenyl-1,2,4-butanetriol as a thick yellow oil.

$^1$H NMR (300 MHz, CDCl$_3$) δ 8.27 (dd, J=1.5, 8.3 Hz, 1H, ArH), 7.60–7.49, 7.32–7.26, (m, 3H, Ar H), 4.80–4.67 (m, 2H, POCH), 4.59 (s, 2H, OCH$_2$O), 3.99 (dd, J=8.6, 13.7 Hz, 1H, CH$_2$P), 3.79 (dd, J=9.3, 13.7 Hz, 1H, CH$_2$P), 3.76–3.68 (m, 1H, H-2), 3.60 (dd, 1H, J=5.1, 10.5 Hz, 1H, H-1), 3.56 (dd, J=4.8, 10.5 Hz, 1H, H-1), 3.33 (s, 3H, OCH$_3$), 2.90–3.01 and 3.17–3.06 (m, 2H, H-4), 2.06–1.98 (m, 2H, H-3), 1.26–1.34 (m, 12H, 4×POCHCH$_3$).

(S)-2-O-(Diisopropyl phosphonomethyl)-1-O-methoxymethyl-4-(2-nitrophenyl)-selenyl-1,2,4-butanetriol obtained previously was dissolved in tetrahydrofuran (15 mL) and treated with hydrogen peroxide (29%, 20 mL) at 0° C. The solution was stirred at 0° C. for 1 hour and then at room temperature for 16 hours. Water (40 mL) and ethyl acetate (100 mL) were added. The aqueous layer was extrated with ethyl acetate (100 mL×2). The combined extracts were washed with saturated sodium bicarbonate (50 mL) and dried over magnesium sulfate. The solvent was evaporated, and the residue was purified by flash chromatography on silica gel (ethyl acetate:hexane=1:1 to 1:0) to give 6.59 g (77% yield) of the title compound as an oil.

$^1$H NMR (300 MHz, CDCl$_3$) δ 5.75–5.63 (m, 1H, H-3), 5.38–5.28 (m, 2H, H-2), 4.78–4.62 (m, 2H, 2×POCH), 4.61 (s, 2H, OCH$_2$O), 4.05–3.96 (m, 1H, H-2), 3.79 (dd, J=9.5, 13.5 Hz, 1H, CH$_2$P), 3.63 (dd, J=8.4, 13.5 Hz, 1H, CH$_2$P), 3.62–3.50 (m, 2H, H-1), 3.57 (s, 3H, OCH$_3$), 1.35–1.28 (m, 12H, 4×POCHCH$_3$).

$^{13}$C NMR (75 MHz, CDCl$_3$) δ 134.5 (C-3), 119.8 (C-4), 96.5 (OCH$_2$O), 82.0 (d, $^3$Jc,p=12 Hz, C-2), 70.8 (t, J=5 Hz, POCH), 69.7 (C-1), 63.0 (d, $^1$Jc,p=169 Hz, CH$_2$P), 55.0 (OCH$_3$), 23.7 (t, J=5 Hz, POCHCH$_3$)

MS (isobutane, DCI): m/e=311 (MH$^+$).

Anal. Calcd for C$_{11}$H$_{23}$O$_5$P: C, 49.62; H, 8.71. Found: C, 49.26; H, 8.54.

(S)-2-O-(Diisopropyl phosphonomethyl)-3-butene-1,2-diol (S)-2-O-(Diisopropyl phosphonomethyl)-1-O-methoxymethyl-3-butene-1,2-diol (3.45 g, 11.12 mmol) and camphorsulfonic acid (0.2 g, 0.8 mmol) were mixed in 45 mL of methanol. The resulting solution was heated at reflux for 5 hours. The solvent was evaporated, and the residue was purified by flash chromatography (ethyl acetate-:petroleum ether=1:1 to 1:0 then ehtyl acetate:methanol 20:1) to give 2.73 g (92%) of the title compound as an oil.

$^1$H NMR (300 MHz, CDCl$_3$) δ 5.69–5.57 (m, 1H, H-3), 5.32–5.23 (m, 2H, H-4), 4.78–4.62 (m, 2H, POCH), 3.82 (dd, J=8.8, 13.5 Hz, 1H, CH$_2$P), 3.56 (dd, J=8.3, 13.5 Hz, 1H, CH$_2$P), 3.92–3.83 (m, 1H, H-2), 3.54 (d, J=4.8 Hz, 2H, H-1), 3.13 (b s, 1H, OH), 1.34–1.26 (m, 12H, 4×POCHCH$_3$).

$^{13}$C NMR (75 MHz, CDCl$_3$) δ 134.1 (C-3), 119.0 (C-4), 84.0 (d, $^3$Jc,p=12 Hz, C-2), 70.5 (d, $^2$Jc,p=6 Hz, POCH), 70.7 (d, $^2$Jc,p=6 Hz, POCH), 64.3 (C-1), 62.8 (d, $^1$Jc,p=170 Hz, CH$_2$P), 23.3 (t, $^3$Jc,p=4 Hz, POCHCH$_3$).

MS (isobutane-DCI): m/e=267 (MH$^+$).

Anal. Calcd for C$_{11}$H$_{23}$O$_5$P: C, 49.62; H, 8.71. Found: C, 49.26; H, 8.54.

(S)-Methanesulfonyl-2-(diisopropyl phosphonomethyl)-3-butene (S)-2-O-(Diisopropyl phosphonomethyl)-3-butene-1,2-diol (2.62 g, 9.84 mmol) was mixed with triethylamine (1.99 g, 19.68 mmol) and 4-dimethylaminopyridine (10 mg) in 30 mL of methylene chloride. To the solution, mesyl chloride (1.35 g, 11.81 mmol) was slowly added at 0° C. The mixture was stirred at 0° C. for 30 min, then at room temperature for additional 30 min. Saturated sodium bicarbonate (50 mL) and methylen chloride (50 mL) were added. The aqueous layer was extracted with methylene chloride (75 mL×2). The combined methylene chloride extracts were dried over magnesium sulfate. The solvent was evaporated, and the residue was purified by flash chromatography (ethyl acetate:petroleum ether=1:1 to 1:0, then ethyl acetate:acetone=5:0 to 5:1) to provide 3.27 g (97% yield) of the title compound as an oil.

$^1$H NMR (300 MHz, CDCl$_3$) δ 5.69–5.58 (m, 1H, H-3), 5.45–5.39 (m, 2H, H-4), 4.77–4.62 (m, 2H, POCH), 4.20 (d, J=5.7 Hz, 2H, H-1), 4.17–4.05 (m, 1H, H-2), 3.77 (dd, J=9.7, 13.6 Hz, 1H, CH$_2$P), 3.57 (dd, J=8.8, 13.6 Hz, 1H, CH$_2$P), 3.05 (s, 3H, SCH$_3$), 1.34–1.23 (m, 12H, 4×POCHCH$_3$).

$^{13}$C NMR (75 MHz, CDCl$_3$) δ 131.8 (C-3), 121.7 (C-4), 80.3 (d, $^3$Jc,p=13 Hz, C-2), 70.8 and 70.7 (t over s, $^2$Jc,p=6 Hz, POCH and C-1), 62.8 (d, $^1$Jc,p=171 Hz, CH$_2$P), 37.33 (SCH$_3$), 23.5 (d, $^3$Jc,p=5 Hz, POCHCH$_3$).

MS (FAB): m/e=344 (MH$^+$).

Anal. Calcd for C$_{12}$H$_{25}$O$_7$PS: C, 41.85; H, 7.32. Found: C, 41.89; H, 7.32.

(S)-2-Amino-6-chloro-9-[2-(diisopropyl phosphonomethoxy)-3-butenyl]purine (S)-Methanesulfonyl-2-(diisopropyl phosphonomethyl)-3-butene (1 g, 2.90 mmol) was mixed with 2-amino-6-chloropurine (0.59 g, 3.48 mmol) and cesium carbonate (1.42 g, 4.35 mmol) in 8 mL of dry N',N'-dimethylformamide. The mixture was stirred at 95°–100° C. under nitrogen atmosphere for 5 hours. The mixture was allowed to cool to room temperature, and filtered. The solid was washed with methylene chloride. The solvent was removed under reduced pressure. The residue was purified by flash chromatography on silica gel (methylene chloride:acetone=3:1 to 0:1; second time, methylene chloride:methanol=15:1) to give 675 mg (56% yield) of the product which crystallized from ethyl acetate-diethyl ether to give 502 mg of the title compound. mp 106°–108° C.

$^1$H NMR (300 MHz, CDCl$_3$) δ 7.90 (s, 1H, H-8), 5.70–5.54 (m, 1H, H-3'), 5.41–5.36 (m, 2H, H-4'), 4.71–4.55 (m, 2H, POCH), 4.27–4.05 (m, 3H, H-1' and H-2'), 3.49 (dd, J=8.5, 13.6 Hz, 1H, CH$_2$P), 1.29–1.19 (m, 12H, POCH CH$_3$).

$^{13}$C NMR (75 MHz, CDCl$_3$) δ 159.3, 154.1, 151.3, 143.8 (G), 133.2 (C-3'), 124.9 (G), 121.9 (C-4'), 80.7 (d, $^3$Jc,p=12 Hz, C-2'), 71.1 (d, $^2$Jc,p=7 Hz, POCH), 62.9 (d, $^1$Jc,p=170 Hz, CH$_2$P), 46.9 (C-1'), 23.7 (d, $^3$Jc,p=4 Hz, POCHCH$_3$).

MS (FAB): m/e=418 (MH$^+$), 456 (MK$^+$).

(S)-9-[(2-phosphonomethoxy)-3-butenyl]guanine ((S)-2'-vinyl-PMEG)

Bromotrimethylsilane (1.82 g, 12.0 mmol) was slowly added to the the solution of (S)-2-amino-6-chloro-9-[2-(diisopropyl phosphonomethoxy)-3-butenyl]purine (0.5 g, 1.2 mmol) in 10 mL of anhydrous acetonitrile under nitrogen atmosphere. The solution was stirred at room temperature for 16 hours. The solvent was evaporated, and the residue was dried in vacuo. To the residue, water (2 mL) and acetone (15 mL) were added. The mixture was stirred at room temperature for 14 hours. The solvent was evaporated, and the residue was washed with acetone and water, and then gently heated at reflux in 20 mL of 10% hydrochloric acid for 6 hours. The solvent was evaporated, and the residue was purified by reverse phase flash chromatography (C18, water:methanol= 1:0 to 10:1). The crude product collected was recrystallized from water to provide 186 mg of the title compound as crystals. The mother liquor was concentrated and crystallized to give additional 62 mg of the product (total 66% yield). mp 275° C. dec.

[α]$^{20}_D$ +50.9° (c 0.46, 1N HCl)

$^1$H NMR (300 MHz, D$_2$O) δ 8.82 (s, 1H, H-8), 5.79–5.68 (m, 1H, H-3'), 5.44–5.37 (m, 2H, H-4'), 4.45–4.36 and 4.30–4.22 (m, 3H, H-2' and H-1'), 3.69 (dd, J=9.3, 13.0 Hz, 1H, CH$_2$P), 3.38 (dd, J=9.3, 13.0 Hz, 1H, CH$_2$P).

$^{13}$C NMR (75 MHz, D$_2$O) δ 161.8, 157.5, 155.0, 144.0, 136.9 (C-3'), 124.2 (C-4'), 117.5 (G), 83.8 (d, $^3$Jc,p=13 Hz, C-2'), 67.8 (d, $^1$Jc,p=158 Hz, CH$_2$P), 50.0 (C-1').

UV (H$_2$O): 252 nm (ε=13,400)

MS (FAB): m/e=316 (MH$^+$)

IR (KBr): 3600–2600 (NH, OH), 1712 (C=O), 1668, 1650 (C=C, C=N), 1106, 1050, 992 (P—O) cm$^{-1}$.

Anal. Calcd for C$_{10}$H$_{14}$N$_5$O$_5$P: C, 38.10; H, 4.48; N, 22.21. Found: C, 37.95; H, 4.41; N, 22.05.

EXAMPLE 2

(R)-9-[2-(phosphonomethyl)-3-butenyl]guanine ((R)-2'-vinyl PMEG

The title, compound was synthesized using the same procedure shown above in Example 1 from (R)-1,2-4-butane triol. The (R)-1,2,4-butane triol was prepared from D-malic acid according to the procedure described in *Can. J. Chem.*, 62, 2146 (1984).

mp 278° C. dec.

[α]$^{20}_D$ −27.2° (c 0.4], H$_2$O).

[α]$^{20}_D$ −46.7° (c 0.30, 1N HCl).

UV (H$_2$O): 252 nm (ε=12,800).

MS (FAB): m/e=316 (MH$^+$).

Anal. Calcd for C$_{10}$H$_{14}$N$_5$O$_5$P: C, 38.10; H, 4.48; N, 22.21. Found: C, 37.89; H, 4.48; N, 21.92.

EXAMPLE 3

(S)-9-[2-(phosphonomethoxy)-3-butenyl]cytosine

(S)-[2-(Diisopropyl phosphonomethoxy)-3-butenyl] cytosine (S)-Methanesulfonyl-2-(diisopropyl phosphonomethyl)-3-butene (1 g, 2.9 mmol) was mixed with cytosine (0.39 g, 3.48 mmol) and cesium carbonate (1.42 g, 4.35 mmol) in 8 mL of dry N',N'-dimethylformamide. The mixture was stirred at 95° C. under nitrogen atmosphere for 4 hours. The mixture was allowed to cool to room temperature, and filtered. The solid was washed with methylene chloride (50 mL). The filtrate was evaporated, and the residue was purified by flash chromatography on silica gel (methylene chloride:methanol=15:1 to 5:1) to give 427 mg (41% yield) of the product which crystallized from ethyl acetate-ether to give 345 mg of the title compound as crystals. mp 137°–138° C.

[α]$^{20}_D$ +84.0° (c 0.96, CH$_2$Cl$_2$).

$^1$H NMR (300 MHz, CDCl$_3$) δ 7.39 (d, J=7.2 Hz, 1H, H-6), 5.77 (d, J=7.2 Hz, 1H, H-5), 5.72, 7.58 (m, 1H, H-3'), 5.46–5.32 (m, 2H, H-4'), 5.74–5.59 (m, 2H, POCH), 4.22–4.10 (m, 2H, H-1'), 3.74 (dd, J=9.5, 13.6 Hz, 1H, CH$_2$P), 3.45 and 3.54–3.41 (dd over m, J=9.5, 13.6 Hz, 2H, CH$_2$P and H-2'), 1.36–1.22 (m, 12H, 4×POCHCH$_3$).

$^{13}$C NMR (300 MHz, CDCl$_3$) δ 166.6 (C-2), 156.9 (C-4), 146.8 (C-6), 133.8 (C-3'), 128.8 (C-4'), 94.2 (C-5), 80.9 (d, $^3$Jc,p= 13.6 Hz, H-2'), 63.0 (d, $^1$Jc, p=170 Hz, CH$_2$P), 70.9 (t, $^2$Jc,p=6 Hz, POCH), 53.1 (1'-C), 23.7 (t, $^3$Jc,p=5 Hz, POCHCH$_3$).

MS (FAB): m/e=360 (MH$^+$), 398 (MK$^+$).

Anal. Calcd for C$_{15}$H$_{26}$N$_3$O$_5$P: C, 50.14; H, 7.29; N, 11.69. Found: C, 49.96; H, 7.12; N, 11.68.

(S)-9-[2-(phosphonomethoxy)-3-butenyl]cytosine

To a solution of (S)-[2-(diisopropyl phosphonomethoxy) -3-butenyl]cytosine (377 mg, 1.05 mmol) in 8 mL of anhydrous acetonitrile, bromotrimethylsilane (1.91 g, 12.6 mmol) was slowly added under nitrogen atmosphere. The solution was stirred at room temperature for 16 hours. The solvent was evaporated, and the residue was dried in vacuo. To the residue, water (2 mL) and acetone (10 mL) were added. The mixture was stirred at room temperature for 24 hours. After the solvent was evaporated, the residue was triturated with acetone, and purified by reverse phase chromatography (C18, water:methanol=10:1 to 5:1). The product collected was recrystallized from methanol and water to provide 193 mg (67% yield) of the title compound as crystals. mp 294° C. dec.

$[\alpha]^{20}{}_D$ +84.0° (c 1.13, $H_2O$)

$^1H$ NMR (300 MHz, $D_2O$) δ 3.38 (dd, J=9.2, 13.2 Hz, 1H, C$\underline{H}_2$P), 3.67 (dd, J=9.3, 13.2 Hz, 1H, C$\underline{H}_2$P), 3.82 (dd, J=7.9, 14.0 Hz, 1H, H-1'), 4.08 and 4.05–4.17 (dd over m, J=3.5, 14.0 HZ, 2H, H-1' and H-2'), 5.37–5.44 (m, 2H, H-4'), 5.66–5.78 (m, 1H, H-3'), 6.11 (d, J=7.7 Hz, 1H, H-5), 7.86 (d, J=7.7 Hz, 1H, 6-CH).

$^{13}C$ NMR (300 MHz, $D_2O$) δ 55.63 (1'-C), 67.85 (d, J=12.4 Hz, $\underline{C}H_2$P), 83.84 (d, J=12.4 Hz, 2'-C), 98.14 (5-C), 123.70 (4'-C), 137.01 (3'-C), 152.42 (6-C), 158.96 (4-C), 167.72 (2-C).

Anal. Calcd for $C_9H_{14}N_3O_5P$: C, 39.28; H, 5.13; N, 15.27. Found: C, 39.10; H, 5.06; N, 15.19.

EXAMPLE 4

(S)-9-[3-azido-2-(phosphonomethoxy)propyl] guanine ((S)-2'-azidomethyl PMEG (R)-3-Azido-1-O-benzyl-2-O-(diisopropyl phosphonomethoxyl)-1,2-propanediol (R)-3-O-Benzyl-2-O-(diisopropyl phosphonomethoxyl)-1-O-(methanesulfonyl)glycerol (15, 9 g, 20.53 mmol) (J. J. Bronson, etc. *J. Med. Chem.* 1989, 32, 1457) and sodium azide (4 g, 61.58 mmol) were mixed in 40 mL of anhydrous N',N'-dimethylformamide. The resulting mixture was stirred at 105° C. for 5 hours. After the solvent was removed under reduced presuure, the residue was added 100 mL of methylene chloride. The mixture was filtered, and the solid was washed with methylene chloride. The filtrate was evaporated, and the residue was purified by flash chromatography on silica gel (methylene chloride:acetone=10:1 to 3:1) to give 6.15 g (78% yield) of the title compound as an oil.

[a]$^{20}{}_D$+7.7° (c 0.42 $CH_2Cl_2$).

$^1H$ NMR (300 MHz, $CDCl_3$) δ 7.35–7.22 (m, 5H, ArH), 4.77–4.62 (m, 2H, POCH), 3.89 (dd, J=8.7, 13.7 Hz, 1H, C$\underline{H}_2$P), 3.83 (dd, J=8.7, 13.7 Hz, 1H, C$\underline{H}_2$P), 3.76–3.69 (m, 1H, H-2), 3.57 (dd, J=5.1, 10.2 Hz, 1H, H-1), 3.50 (dd, J=5.5, 10.2 Hz, 1H, H-1), 3.50 (dd, J=4.2, 13.0 Hz, 1H, H-3), 3.43 (dd, J=6.1, 13.0 Hz, 1H, H-3), 1.25–1.31 (m, 12H, 4×POCHC$\underline{H}_3$).

$^{13}C$ NMR (75 MHz, $CDCl_3$) δ 137.9, 128.6, 127.9, 127.8, 79.7 (d, $^3$Jc,p=10 Hz, C-2), 73.4 (O$\underline{C}H_2$Ph), 71.1 (d, $^2$Jc,p=4 Hz, PO$\underline{C}H$), 69.3 (C-1), 65.0 (d, $^1$Jc,p=168 Hz, $\underline{C}H_2$P), 51.8 (C-3), 23.8 (d, $^3$Jc,p=4 Hz, POCH$\underline{C}H_3$), 23.6 (d, $^3$Jc,p=4 Hz, POCH$\underline{C}H_3$).

Anal. Calcd for $C_{17}H_{28}N_3O_5P$: C, 52.98; H, 7.32; N, 10.90. Found: C, 52.64; H, 7.20; N, 10.86.

(R)-3-Azido-2-O-(diisopropyl phosphonomethoxyl)-1,2-propanediol (R)-3-Azido-1-O-benzyl-2-O-(diisopropyl phosphonomethoxyl)-1,2-propanediol (6.15 g, 15.96 mmol) was dissolved in 35 mL of anhydrous methylene chloride under nitrogen atmosphere. To this solution, boron trichloride (1M in methylene chloride) (48 mL, 48 mmol) was slowly added at −78° C. The mixture was stirred at −78° C. for 4 hour, and then saturated aqueous sodium bicarbonate (100 mL) and methylene chloride (150 mL) were added. The aqueous layer was separated and extrated with methylene chloride (150 mL×2). The combined methylene chloride extracts were dried over magnesium sulfate. Filtration and concentration under reduced pressure gave a residue which was purified by flash chromatography on silica gel (methylene chloride:acetone=5:1 to 1:1) to provide 4.39 q (93% yield) of the title compound as an oil.

$^1H$ NMR (300 MHz, $CDCl_3$) δ 4.82–4.65 (m, 2H, POC $\underline{H}$), 4.05 (dd, J=6.9, 14.0 Hz, 1H, C$\underline{H}_2$P), 3.77 (dd, J=8.9, 14.0 Hz, 1H, C$\underline{H}_2$P), 3.72 (dd, J=2.1, 11.7 Hz, 1H, H-1), 3.56 and 3.64–3.57 (dd over m, J=5.4, 11.7 Hz, 2H, H-1 and H-2), 3.4 (dd, J=7.3, 12.9 Hz, 1H, H-3), 3.23 (dd, J=3.9, 12.9 Hz, 1H, H-3), 1.34–1.28 (m, 12H, 4×POCHC$\underline{H}_3$).

$^{13}C$ NMR (75 MHz, $CDCl_3$) δ 82.5 (d, $^3$Jc,p=9 Hz, C-2), 71.7 (d, $^2$Jc,p=7 Hz, PO$\underline{C}H$), 71.2 (d, $^2$Jc,p=7 Hz, PO $\underline{C}H$), 64.9 (d, $^1$Jc,p=170 Hz, $\underline{C}H_2$P), 61.4 (C-1), 51.5 (C-3), 23.6 (d, $^3$Jc,p=5 Hz, POCH$\underline{C}H_3$), 23.4 (d, $^3$Jc,p=5 Hz, POCH$\underline{C}H_3$).

MS (isobutane, DCI): m/e=296 (MH$^+$).

(R)-3-Azido-2-O-(diisopropyl phosphonomethoxyl)-1-O-methanesulfonyl-1,2-propanediol To a solution of (R)-3-azido-2-O-(diisopropyl phosphonomethoxyl)-1,2-propanediol (6.4 g, 21.67 mmol) and triethylamine (4.39 g, 43.4 mmol) in methylene chloride (100 mL), methanesulfonylchloride (2.98 g, 26 mmol) was slowly added at 0° C. under nitrogen atmosphere. The resulting solution was stirred at 0° C. for 1 hour and then slowly warmed to room temperature during an hour. Water (100 mL) was added to the solution. The aqueous was separated and extrated with methylene chloride (150 mL×2). The combined methylene chloride extracts were dried over magnesium sulfate. The solvent was evaporated, and the residue was purified by flash chromatography on silica gel (methylene chloride:acetone=10:1 to 3:1) to provide 7.21 g (87% yield) of the title compound as an oil.

$[\alpha]^{20}{}_D$ +2.3° (c 16.76, $CH_2Cl_2$)

$^1H$ NMR (300 MHz, $CDCl_3$) δ 4.78–4.63 (m, 2H, POC$\underline{H}$), 4.32 (dd, J=4.6, 11.2 Hz, 1H, H-1), 4.26 (dd, J=5.1, 11.2 Hz, 1H, H-1), 3.86 and 3.87–3.81 (d over m, J=8.6 Hz, 3H, C$\underline{H}_2$P and H-2), 3.50 (dd, J=4.7, 13.1 Hz, 1H, H-3), 3.42 (dd, J=5.7, 13.1 Hz, 1H, H-3), 3.05 (s, 3H, SC$\underline{C}H_3$), 1.30 (d, J=6.2, Hz, 12H, 4×POCHC$\underline{H}_3$).

$^{13}C$ NMR (75 MHz, $CDCl_3$) δ 78.1 (d, 3Jc,p=10 Hz, C-2), 71.3 (t, $^2$Jc,p=6 Hz, PO$\underline{C}H$), 65.2 (d, $^1$Jc,p=169 Hz, $\underline{C}H_2$P), 50.5 (C-3), 37.2 (S$\underline{C}H_3$), 23.6 (t, $^3$Jc,p=5 Hz, POCH $\underline{C}H_3$).

MS (isobutane, DCI): m/e=374 (MH$^+$).

Anal. Calcd for $C_{11}H_{24}N_3O_7PS$: C, 35.39; H, 6.48; N, 11.25. Found: C, 35.15; H, 6.29; N, 11.09.

(S)-2-Amino-9-[3-azido-2-(diisopropyl phosphonomethoxy)]propyl]-6-chloro-purine (19)

(R)-3-Azido-2-O-(diisopropyl phosphonomethyl)-1-O-methanesulfonyl-1,2-propanediol (2.0 g, 5.22 mmol) was mixed with 2-amino-6-chloropurine (3.40 g, 10.43 mmol) and cesium carbonate (3.92 g, 12.0 mmol) in 15 mL of anhydrous N',N'-dimethylformamide. The mixture was stirred at 90° C. under nitrogen atmosphere for 3 hours, then allowed to cool to room temperature, and filtered. The solvent was removed under reduced pressure. The residue was purified by flash chromatography on silica gel twice (first time, methylene chloride:acetone=3:1 to 0:1;second time, methylene chloride:methanol=15:1 to 10:1) to give a thick oil which crystallized from ethyl acetate and diethyl ether to give 1.34 g (58%) of the title compound as crystals. mp 126°–128° C.

$[\alpha]^{20}_D$ −9.9° (c 0.89, MeOH)

$^1$H NMR (300 MHz, CDCl$_3$) δ 7.87 (s, 1H, H-8), 5.45 (br s, 2H, NH$_2$), 4.72–4.56 (m, 2H, 2×POCH), 4.26 (dd, J=4.3, 14.6 Hz, 1H, H-1'), 4.18 (dd, J=5.6, 14.6 Hz, 1H, H-1'), 3.91–3.82 (m, 1H, H-2'), 3.71 (dd, J=8.9, 13.9 Hz, 1H, CH$_2$P), 3.79 (dd, J=8.6, 13.9 Hz, 1H, CH$_2$P), 3.43 (dd, J=5.1, 13.2 Hz, 1H, H-3'), 3.25 (dd, J=4.9, 13.2 Hz, 1H, H-3'), 1.27–1.19 (m, 12H, 4×POCHCH$_3$).

$^{13}$C NMR (75 MHz, CDCl$_3$) δ 159.4, 154.3, 151.4, 143.6, 124.8, 77.6 (d, $^3$Jc,p=12 Hz, C-2'), 71.2 (t, $^2$Jc,p=4 Hz, POCH), 65.0 (d, $^1$Jc,p=170 Hz, CH$_2$P), 47.1 and 45.4 (C-1' and C-4'), 30.7 (C-3'), 23.7 (d, $^3$Jc,p=4 Hz, POCHCH$_3$).

Anal. Calcd for C$_{15}$H$_{24}$ClN$_8$O$_4$PS: C, 40.32; H, 5.41; N, 25.08. Found: C, 40.36; H, 5.52; N, 24.94.

(S)-9-[3-azido-2-(phosphonomethoxy)propyl] guanine ((S)-2'-azidomethyl PMEG (S)-2-Amino-9-[3-azido-2-(diisopropyl phosphonomethoxy)]propyl]-6-chloro-purine (1.0 g, 2.24 mmol) was dissolved in 10 mL of acetonitrile and treated slowly with bromotrimethylsilane (3.43 g, 22.40 mmol) under nitrogen atmosphere. The reaction mixture was allowed to stir at room temperature for 14 hours, and the solvent was removed under reduced pressure. The residue was dried in vacuo and then treated with acetone (8 mL) and water (2 mL). The resulting mixture was stirred at room temperature for 6 hours. The mixture was filtered and the residue was washed with acetone and water. The resulting solid was heated gently at reflux in 10 mL of 2N HCl for 5 hours. The solution was evaporated under reduced pressure, and the residue was recrystallized from water to give 533 mg of the title compound as pale yellow crystals. The mother liquor was concentrated to provide an additional 72 mg of the title compound (total 79% yield): mp 263° C. dec.

$[\alpha]^{20}_D$ −18.4° (c 0.38, 1N HCl).

$^1$H NMR (300 MHz, D$_2$O) δ 7.69 (s, 1H, H-8), 4.13 (dd, J=5.3, 14.8 Hz, 1H, H-1'), 4.06 (dd, J=5.3, 14.8 Hz, 1H, H-1'), 3.79–3.74 (m, 1H, H-2'), 3.46–3.40 (m, 2H, CH$_2$P and H-3'), 3.34 (dd, J=9.4, 12.2 Hz, 1H, CH$_2$P), 3.18 (dd, J=4.7, 13.3 Hz, 1H, H-3').

$^{13}$C NMR (75 MHz, D$_2$O-NaOD) δ 171.7, 164.6, 155.1, 142.7, 120.5, 80.8 (d, $^3$Jc,p=11 Hz, C-2'), 71.1 (d, $^1$Jc,p=151 Hz, CH$_2$P), 53.7 (C-3'), 46.5 (C-1').

IR (KBr): 3600–2600 (NH, OH), 2110 (N$_3$), 1712 (C=O), 1685, 1650 (C=C, C=N), 1106, 1000, 958 (P-O) cm$^{-1}$

MS (FAB): m/e=345 (MH$^+$)

Anal. Calcd for C$_9$H$_{13}$N$_8$O$_5$P·½H$_2$O: C, 30.60; H, 4.00; N, 31.72. Found: C, 30.67; H, 3.79; N, 31.83.

EXAMPLE 5

(R)-9-[3-azido-2-(phosphonomethoxy)propyl] guanine ((R)-2'azidomethyl PMEG (R)- [3-Azido-2-(phosphonomethoxy)propyl] guaninine The title compound was prepared using the procedure described in Example 4 but starting with the (S)-chiral starting material, (S)-3-O-Benzyl-2-O-(diisopropyl phosphonomethoxyl)-1-O-(methanesulfonyl)glycerol.

$[\alpha]^{20}_D$ +16.7° (c 0.63, 1N HCl).

MS (FAB) m/e=345 (MH$^+$)

Anal. Calcd for C$_9$H$_{13}$N$_8$O$_5$P·⅔H$_2$O: C, 30.34; H, 4.05; N, 31.45. Found: C, 30.41; H, 3.84; N, 31.40.

EXAMPLE 6

(S)-9-[3-Azido-2-phosphonomethoxy)propyl] cytosine (S)-[3-Azido-2-[(diisopropyl phosphonomethoxy) propyl]cytosine (R)-3-Azido-2-O-(diisopropyl phosphonomethoxy)-1-O-methanesulfonyl-1,2-propanediol (2.0 g, 5.22 mmol) was mixed with cytosine (0.7 g, 6.26 mmol) and cesium carbonate (3.40 g, 10.43 mmol) in 15 mL of anhydrous N',N'-dimethylformamide. The mixture was stirred at 90° C. under nitrogen atmosphere for 3 hours, the allowed to cool to room temperature, and filtered. The solvent was removed under reduced pressure. The residue was purified by flash chromatography on silica gel (methylene chloride:methanol= 15:1 to 5:1) to give 1.00 g (49%) of the title compound as a thick oil.

$[\alpha]^{20}_D$ 37.6° (C 2.41, MeOH).

$^1$H NMR (300 MHz, CDCl$_3$) δ 7.43 (d, J=7.2 Hz, 1H, H-5), 5.69 (d, J=7.2 Hz, 1H, H-6), 4.75–4.61 (m, 2H, 2×POCH), 4.03 (dd, J=3.7, 13.5 Hz, 1H, H-1'), 3.86 and 3.87–3.82 (dd over m, J=8.7, 13.6 Hz, 2H, CH$_2$P and H-2'), 3.74 (dd, J=6.7, 13.5 Hz, 1H, H-1'), 3.69 (dd, J=9.4, 13.6 Hz, 1H, CH$_2$P), 3.62 (dd, J=3.3, 13.3 Hz, 1H, H-3'), 3.26 (dd, J=5.2, 13.3 Hz, 1H, H-3'), 1.30 (d, J=6.3 Hz, 2×POCH CH$_3$), 1.28 (d, J=6.1 Hz, 2×POCHCH$_3$).

$^{13}$C NMR (75 MHz, CDCl$_3$) δ 166.7, 157.1, 146.7, 94.8, 79.0 (d, $^3$Jc,p=11 Hz, C-2'), 71.4 (d, $^2$Jc,p=6 Hz, POCH), 71.3 (d, $^2$Jc,p=6 Hz, POCH), 65.2 (d, $^1$Jc,p=169 Hz, CH$_2$P), 51.4, 50.6 (C-1' and C-2'), 23.7 (t, $^3$Jc,p=5 Hz, POCHCH$_3$).

MS (isobutane, DCI): m/e=389 (MH$^+$).

(S)-9- [3-Azido-2-phosphonomethoxy)propyl] cytosine (S)-[3-Azido-2-(diisopropyl phosphonomethoxy)propyl] cytosine (0.85 g, 2.2 mmol) was dissolved in 9 mL of anhydrous acetonitrile and treated slowly with bromotrimethylsilane (4.06 g, 37.7 mmol) under nitrogen atmosphere. The reaction mixture was allowed to stir at room temperature for 12 hours, and the solvent was removed under reduced pressure. The residue was dried in vacuo and then treated with acetone (10 mL) and water (2 mL). The resulting mixture was stirred at room temperature for 6 hours. The mixture was filtered and washed with acetone and water. The solids collected were recrystallized from water-methanol to give 370 mg (55% yield) of the title compound as white crystals. mp 210° C. dec.

$[\alpha]^{20}_D$ −75 0° (c 0.32, 1N HCl)

$^1$H NMR (300 MHz, D$_2$O) δ 7.73 (d, J=7.7 Hz, 1H, H-5), 6.00 (d, J=7.7 Hz, 1H, H-6), 4.00 (dd, J=6.6, 17.7 Hz, 1H, H-1'), 3.81–3.72 (m, 2H, H-1' and H-2'), 3.66 (dd, J=9.0, 13.1 Hz, 1H, CH$_2$P), 3.57 (dd, J=3.9, 13.5 Hz, 1H, H-3'), 3.42 (dd, J=9.5, 13.1 Hz, 1H, CH$_2$P), 3.28 (dd, J=3.6, 13.5 Hz, 1H, H-3').

$^{13}$C NMR (75 MHz, D$_2$O) δ 170.0, 151.7, 150.7, 95.2, 78.6 (d, $^3$Jc,p=12 Hz, C-2'), 66.9 (d, $^1$Jc,p=158 Hz, CH$_2$P), 51.2, 51.0 (C-1' and C-2').

IR (KBr): 3500–2500 (OH, NH), 2110 ($N_3$), 1722 (C=O), 1680 (C=N, C=C), 1116, 1060, 930 (P-O) cm$^{-1}$

MS (FAB): m/e=305 (MH$^+$).

Anal. Calcd for $C_8H_{13}N_6O_5P$: C, 31.59; H, 4.31; N, 27.62. Found: C, 31.37; H, 4.52; N, 27.90.

EXAMPLE 7

(R)-9-[3-Azido-2-phosphonomethoxy)propyl] cytosine

The title compound was prepared using procedures of Example 6 but starting with the starting material (S)-3-azido-2-O-(diisopropyl phosphonomethoxy)-1-O-methanesulfonyl-1,2-propanediol.

$[\alpha]^{20}_D$ +60.6° (c 0.46, 1N HCl)

MS (FAB): m/e=305 (MH$^+$).

Anal. Calcd for $C_8H_{13}N_6O_5P \cdot \frac{1}{2}H_2O$: C, 30.93; H, 4.44; N, 27.06. Found: C, 30.83; H, 4.41; N, 27.07.

EXAMPLE 8

(S)-9-[3-Azido-2-phosphonomethoxy)propyl] thymine (S)-3-Azido-2-[(diisopropyl phosphonomethoxy) propyl]-4-O-methylthymine (R)-3-Azido-1-O-methanesulfonyl-2-O-(diisopropyl phosphonomethyl)-1,2-propanediol (1 g, 2.61 mmol) was mixed with 4-O-methylthymine (0.44 g, 3.13 mmol) and cesium carbonate (1.27 g, 3.91 mmol) in 10 mL of anhydrous N',N'-dimethylformamide. The mixture was stirred at 95° C. under nitrogen atmosphere for 5 hours.

The mixture was allowed to cool to room temperature, and filtered. The solid was washed with methylene chloride. The filtrate was evaporated and the residue was purified by flash chromatography on silica gel (methylene chloride:methanol=10:1 to 5:1) to give 270 mg (27% yield) of the title compound as a thick oil.

$^1$H NMR (300 MHz, CDCl$_3$) δ 7.41 (S, 1H, H-6), 4.63–4.78 (m, 2H, 2×POCH), 4.08 (dd, J=3.4, 13.4 Hz, H-1'), 3.96 (s, 3H, OCH$_3$), 3.96–3.80 (m, 3H, H-1', H-2' and CH$_2$P), 3.71–3.62 (m, 2H, CH$_2$P and H-3'), 3.26 (dd, J=5.2, 13.5 Hz, H-3'), 1.93 (s, 3H, CH$_3$), 1.32–1.27 (m, 12H, 2×POCHCH$_3$).

$^{13}$C NMR (75 MHz, CDCl$_3$) δ 171.1 (C-2), 156.8 (C-4), 145.8 (C-6), 104.2 (C-5), 78.8 (d, $^3$Jc,p=10 Hz, C-2'), 71.0 (d, $^2$Jc,p=7 Hz, POCH), 70.9 (d, $^2$Jc,p=7 Hz, POCH), 65.2 (d, $^1$Jc,p=169 Hz, CH$_2$P), 54.2 (OCH$_3$), 51.3 and 50.6 (C-1' and C-3'), 23.4 (t, $^3$Jc,p=4 Hz, POCHCH$_3$), 11.4 (5-CH$_3$).

MS (isobutane, DCI): m/e=417 (MH$^+$).

(S)-9-[3-Azido-2-phosphonomethoxy)propyl] thymine (S)-[3-Azido-2-[(diisopropyl phosphonomethoxy)propyl] -4-O-methylthymine (200 mg, 0.52 mmol) was dissolved in 5 mL of acetonitrile and treated slowly with bromotrimethylsilane (1.19 g, 7.8 mmol) under nitrogen atmosphere. The reaction mixture was allowed to stir at room temperature for 14 hours, and the solvent was removed under reduced pressure. The residue was dried in vacuo and then treated with acetone (5 mL) and water (1 mL). The resulting mixture was stirred at room temperature for 16 hours. The solvent was evaporated, and the residue was purified by reverse phase chromatography (C18, water:methanol=10:0 to 5:1) to provide 103 mg of the title compound as a white foam.

$[\alpha]^{20}_D$ −25.0° (c 0.22, H$_2$O). $^1$H NMR (300 MHz, CD$_3$OD) δ 7.20 (s, 1H, H-6), 3.77 (dd, J=3.1, 13.9 Hz, 1H, H-1'), 3.68 (dd, J=8.9, 13.4 Hz, 1H, CH$_2$P), 3.64–3.57 (m, 1H, H-2'), 3.57–3.47 (m, 2H, H-1' and CH$_2$P), 3.35 (dd, J=4.0, 13.3 Hz, 1H, H-3'), 3.11 (dd, J=4.9, 13.3 Hz, 1H, H-3'), 1.61 (s, 3H, CH$_3$).

$^{13}$C NMR (75 MHz, CD$_3$OD) δ 167.7 (C-2), 153.8 (C-4), 145.0 (C-6), 111.2 (C-5), 80.7 (d, $^3$Jc,p=11 Hz, C-2'), 66.7 (d, $^1$Jc,p=166 Hz, CH$_2$P), 52.6 and 50.6 (C-1' and C-3'), 12.4 (5-CH$_3$).

IR (KBr): 3600–2600 (NH, OH), 2108 ($N_3$), 1678 (C=O), 1608 (C=C, C=N), 1114, 1004, 940 (P—O) cm$^{-1}$.

MS (FAB): m/e=320 (MH$^+$).

EXAMPLE 9

(R)-9-[3-Azido-2-phosphonomethoxy)propyl] thymine

The title compound can be prepared using the procedure of Example 8 but with the (S) chiral starting material.

EXAMPLE 10

Aminomethyl Compounds of Examples 4–9

The aminomethyl analogs of the compounds of Examples 4, 5, 6, 7, 8 and 9 can be prepared by reduction of the compounds of Examples 4–9.

EXAMPLE 11

(S)-9-[4-azido-2-(phosphonomethoxy)butyl]guanine (S)-azidoethyl-PMEG (S)-2-O-(Diisopropylpbosphonomethyl)-4-O-methanesulfonyl-1-O-methoxymethyl-1,2,4-butanetriol Mesyl chloride (2.14 g, 18.64 mmol) was slowly added to a solution of (S)-2-O-(diisopropylphosphonomethyl)-1-O-methoxymethyl-1,2,4-butanetriol in 50 mL of methylene chloride at 0° C. under nitrogen atmosphere. After the mixture was stirred at 0° C. for 5 min, triethylamine was added during 30 min. The mixture was stirred at 0° C. for 30 min and saturated sodium bicarbonate (50 mL) was added. The aqueous solution was extracted with methylene chloride (50 mL×2). The combined extracts were dried over magnesium sulfate. Filtration and evaporation gave a residue which was purified by flash chromatography on silica gel (methylene chloride:acetone=5:1 to 2:1) to provide 6.22 g (99% yield) of the title compound as an oil.

$[\alpha]^{20}_D$ −17.9° (c 0 67, MeOH)

$^1$H NMR (300 MHz, CDCl$_3$) δ 4.62–4.88 (m, 2H, 2×POC H), 4.58 (s, 2H, OCH$_2$O), 4.28–4.42 (m, 2H, H-4), 3.95 (dd, J=8.8, 13.7 Hz, 1H, CH$_2$P), 3.73 and 3.67–3.74 (dd over m, J=9.3, 13.7 Hz, 2H, CH$_2$P and H-2), 3.51–3.61 (m, 2H, H-1), 3.32 (s, 3H, OCH$_3$), 3.00 (s, 3H, CH$_3$SO$_2$), 1.83–2.30 (m, 2H, H-3), 1.27–1.31 (m, 12H, POCHCH$_3$).

$^{13}$C NMR (75 MHz, CDCl$_3$) δ 96.3 (OCH$_2$O), 76.6 (d, $^3$Jc,p=12 Hz, C-2), 70.7 (d, $^2$Jc,p=7 Hz, POCH), 70.6 (d, $^2$Jc,p=7 Hz, POCH), 68.7 (C-4), 66.4 (1-C) 64.5 (d, $^1$Jc,p= 170 Hz, CH$_2$P), 54.9 (OCH$_3$), 36.71 (SCH$_3$), 31.2 (C-3), 23.5 (t, $^3$Jc,p=4 Hz, POCHCH$_3$).

MS (isobutane, DCI): m/e=407 (MH$^+$)

Anal. Calcd for $C_{14}H_{31}O_9PS$: C, 41.37; H, 7.69. Found: C, 41.54; H, 7.39.

(S)-4-Azido-2-O-(diisopropyl phosphonomethoxy)-1,2-butanediol (S)-2-O-(Diisopropylphosphonomethyl)-4-O-methanesulfonyl-1-O-methoxymethyl-1,2,4-butanetriol (5 g, 12.30 mmol) and sodium azide (1.2 g, 18.45 mmol) in 10 mL of anhydrous N',N'-dimethylformamide was stirred at 130° C. under nitrogen atmosphere for 3 hours. The mixture was cooled to room temperature and filtered. The filtrate was evaporated, and the residue was purified by flash chromatography (methylene chloride:methanol=20:1 to 10:1) to give (S)-4-azido-1-O-methoxymethyl-2-O-(diisopropylphosphonomethoxy)]-1,2-butanediol.

$^1$H NMR (300 MHz, CDCl$_3$) δ 4.79–4.60 (m, 2H, POCH), 4.59 (s, 2H, OCH$_2$O), 3.96 (dd, J=8.7, 13.6 Hz, 1H, CH$_2$P), 3.74 (dd, J=9.5, 13.6 Hz, 1H, CH$_2$P), 3.69–3.61 (m, 1H, H-2), 3.55 (d, J=4.5 Hz, 2H, H-1), 3.43 (t, J=6.8 Hz, 2H, H-4), 3.33 (s, 3H, OCH$_3$), 1.80–1.73 (m, 2H, H-3), 1.30 (d, J=6.2 Hz, 6H, POCHCH$_3$), 1.29 (d, J=6.2 Hz, 6H, POCHCH$_3$).

$^{13}$C NMR (75 MHz, CDCl$_3$) δ 96.5 (OCH$_2$O), 77.7 (d, $^3$Jc,p=12 Hz, C-2), 70.8 (t, $^2$Jc,p=6 Hz, POCH), 69.1 (C-1), 64.7 (d, $^1$Jc,p=170 Hz, CH$_2$P), 55.1 (OCH$_3$), 47.4 (C-4), 30.8 (C-3), 23.6 (t, $^3$Jc,p=4 POCHCH$_3$).

MS (FAB): m/e=354 (MH$^+$).

Anal. Calcd for C$_{13}$H$_{28}$N$_3$O$_6$P: C, 44.19; H,7.99; N, 11.89. Found: C,43.90; H, 8.02; N, 11.50.

(S)-4-Azido-1-O-methoxymethyl-2-O(diisopropyl phosphonomethoxy)]-1,2-butanediol obtained previously was treated with 50 mL of methanol and 0.5 g of camphorsulfonic acid. The resulting mixture was heated at reflux for 16 hours. The solvent was evaporated, and the residue was purified by flash chromatography on silica gel (methylene chloride:acetone=5:1 to 2:1) to provide 2.53 g (67%) yield of the title compound as an oil.

$^1$H NMR (300 MHz, CDCl$_3$) δ 4.81–4.63 (m, 2H, POCH), 3.91 (dd, J=7.2, 14.1 Hz, 1H, CH$_2$P), 3.73 and 3.76–3.68 (dd over m, J=9.1, 14.1 Hz, 2H, CH$_2$P and H-1), 3.58–3.46 (m, 2H, H-2 and H-1), 3.40 (d, J=5.9 Hz, 1H, H-4), 3.37 (d, J=5.9 Hz, 1H, H-4), 1.88–1.60 (m, 2H, H-3), 1.31 (d, J=4.8 Hz, 6H, 2×POCHCH$_3$), 1.29 (d, J=4.8 Hz, 6H, 2×POCHCH$_3$)

$^{13}$C NMR (75 MHz, CDCl$_3$) δ 80.8 (d, $^3$Jc,p=9 Hz, C-2), 71.5 (d, $^2$Jc,p=7 Hz, POCH), 71.1 (d, $^2$Jc,p=7 Hz, POCH), 64.7 (d, $^1$Jc,p=170 Hz, CH$_2$P), 63.6 (C-1), 47.6 (C-4), 30.4 (C-3), 23.6 (m, POCHCH$_3$).

MS (DCI, isobutene): m/e=309 (MH$^+$).

IR (neat): 3388 (OH), 2098 (N$_3$), 1240 (P=O), 1106 (C—O), 994 (P—O—C).

Anal. Calcd for C$_{11}$H$_{24}$N$_3$O$_5$P: C, 42.71; H,7.82; N, 13.58. Found: C,42.74; H, 7.87; N, 13.32.

(S)-4-Azido-2-O-(diisopropyl phosphonomethoxy)-1-O-methanesulfonyl-1,2-butanediol To a solution of (S)-4-azido-2-O-[(diisopropylphosphonomethoxy)]-1,2-butanediol (2.50 g, 8.08 mmol) in 30 mL of methylene chloride, mesyl chloride (1.11 g, 9.7 mmol) was slowly added at 0° C. Triethylamine (1.64 g, 16.16 mmol) was added during 30 min. The mixture was stirred at 0° C. for 30 min, and saturated sodium bicarbonate (40 mL) was added. The aqueous layer was extracted with methylene chloride (75 mL×2). The combined extracts were dried over magnesium sulfate. The solvent was evaporated, and the residue was purified by flash chromatography on silica gel (methylene chloride:acetone=5:1 to 2:1) to give 3.05 g (97% yield) of the title compound as an oil.

$^1$H NMR (300 MHz, CDCl$_3$) δ 4.80–4.64 (m, 2H, 2×POCH), 4.34 (dd, J=3.6, 11.2 Hz, 1H, H-1), 4.26 (dd, J=5.3, 11.2 Hz, 1H, H-1), 3.87 (dd, J=8.8, 13.6 Hz, 1H CH$_2$P), 3.75 and 3.83–3.74 (dd and m, J=9.7 13.6 Hz, 2H, CH$_2$P and H-2), 3.48 (t, J=6.6 Hz, 2H, H-4), 3.06 (s, 3H, SCH$_3$), 1.90–1.68 (m, 2H, H-3), 1.32 (d, J=6.2, Hz, 6H, 2×POCHCH$_3$), 1.31 (d, J=6.2, Hz, 6H, 2×POCHCH$_3$).

$^{13}$C NMR (75 MHz, CDCl$_3$) δ 76.7 (d, $^3$Jc,p=12 Hz, C-2), 71.1 (d, $^2$Jc,p=6 Hz, POCH), 71.0 (d, $^2$Jc,p=6 Hz, POCH), 69.9 (C-1), 65.1 (d, $^1$Jc,p=170 Hz, CH$_2$P) 47.0 (C-4), 37.3 (SCH$_3$), 30.2 (C-3), 23.7 (d, $^3$Jc,p 5 Hz POCHCH$_3$)

MS (DCI, isobutene): m/e=309 (MH$^+$).

IR (neat): 3388 (OH), 2098 (N$_3$), 1240 (P=O), 1106 (C—O), 994 (P—O—C).

Anal. Calcd for C$_{11}$H$_{24}$N$_3$O$_5$P: C, 42.71; H,7.82; N, 13.58. Found: C,42.74 ; H, 7.87; N, 13.32.

(S)-4-Azido-2-O-(diisopropyl phosphonomethoxy)-1-O-methanesulfonyl-1,2-butanediol To a solution of (S)-4-azido-2-O-[(diisopropylphosphonomethoxy)]-1,2-butanediol (2.50 g, 8.08 mmol) in 30 mL, of methylene chloride, mesyl chloride (1.11 g, 9.7 mmol) was slowly added at 0° C. Triethylamine (1.64 g, 16.16 mmol) was added during 30 min. The mixture was stirred at 0° C. for 30 min, and saturated sodium bicarbonate (40 mL) was added. The aqueous layer was extracted with methylene chloride (75 mL×2). The combined extracts were dried over magnesium sulfate. The solvent was evaporated, and the residue was purified by flash chromatography on silica gel (methylene chloride:aceton=5:1 to 2:1) to give 3.05 g (97% yield) of title compound as an oil.

$^1$H NMR (300 MHz, CDCl$_3$) δ 4.80–4.64 (m, 2H, 2×POCH), 4.34 (dd, J=3.6, 11.2 Hz, 1H, H-1), 4.26 (dd, J=5.3, 11.2 Hz, 1H, H-1), 3.87 (dd, J=8.8, 13.6 Hz, 1H CH$_2$P), 3.75 and 3.83–3.74 (dd and m, J=9.7 13.6 Hz, 2H, CH$_2$P and H-2), 3.48 (t, J=6.6 Hz, 2H, H-4), 3.06 (s, 3H, SCH$_3$), 1.90–1.68 (m, 2H, H-3), 1.32 (d, J=6.2, Hz, 6H, 2×POCHCH$_3$), 1.31 (d, J=6.2, Hz, 6H, 2×POCHCH$_3$).

$^{13}$C NMR (75 MHz, CDCl$_3$) δ 76.7 (d, $^3$Jc,p=12 Hz, C-2), 71.1 (d, $^2$Jc,p=6 Hz, POCH) 71.0 (d, $^2$Jc,p=6 Hz, POCH) 69.9 (C-1), 65.1 (d $^1$Jc,p=170 Hz, CH$_2$P). 47.0 (C-4), 37.3 (SCH$_3$), 30.2 (C-3), 23.7 (d, $^3$Jc,p=5 Hz, POCHCH$_3$).

MS (DCI, isobutene): m/e=374 (MH$^+$).

(S)-2-Amino-9-[4-azido-2-(diisopropyl phosphonomethoxy)butyl]-6-chloropurine (S)-2-Amino-9-[4-azido-2-(diisopropyl phosphonomethoxy)butyl]-6-chloropurine (1.0 g, 2.58 mmol) was mixed with 2-amino-6-chloropurine (0.53 g, 3.10 mmol) and cesium carbonate (1.26 g, 3.87 mmol) in 10 mL of dry N',N'-dimethylformamide. The mixture was stirred at 95°–100° C. under nitrogen atmosphere for 4 hours. The mixture was allowed to cool to room temperature, and filtered. The solid was washed with methylene chloride. The solvent was removed under reduced pressure and the residue was purified by flash chromatography on silica gel (methylene chloride:acetone=3:1 to 0:1; second time, methylene chloride:methanol=15:1 to 10:1) to give 681 mg (57% yield) of the title compound as a thick oil.

$^1$H NMR (300 MHz, CDCl$_3$) δ 7.94 (s, 1H, H-8), 5.14 (br s, 2H, NH$_2$), 4.78–4.63 (m, 2H,2×POCH), 4.30 (dd, J=3.5, 14.7 Hz, 1H, H-1'), 4.15 (dd, J=5.2, 14.7 Hz, 1H, H-1'), 3.89–3.81 (m, 1H, H-2'), 3.76 (dd, J=9.5, 13.5 Hz, 1H, CH$_2$P), 3.72 (dd, J=9.5, 13.5 Hz, 1H, CH$_2$P), 3.47 (t, J=5.9 Hz, 2H, H-4'), 1.78–1.50 (m, 2H, H-3'), 1.32–1.25 (m, 12 Hz, 4×POCHCH$_3$).

$^{13}$C NMR (75 MHz, CDCl$_3$) δ 159.4, 154.3, 151.4, 143.6, 124.8, 77.6 (d, 3Jc,p=12 Hz, C-2'), 71.2 (t, 2Jc,p=4 Hz, PO

CH), 65.0 (d, $^1J_{C,P}$=170 Hz, CH$_2$P), 47.1 and 45.4 (C-1' and C-4'), 30.7 (C-3'), 23.7 (d, $^3J_{C,P}$=4 Hz, POCHCH$_3$).

MS (DCI, isobutene): m/e=461 (MH$^+$).

Anal. Calcd for C$_{16}$H$_{26}$ClN$_8$O$_4$P: C, 41.70; H, 5.68; N, 24.31. Found: C, 41.55; H, 5.50; N, 24.00.

(S)-9-[4-azido-2-(phosphonomethoxy)butyl]guanine (S)-azidoethyl-PMEG

Bromotrimethylsilane (1.99 g, 13 mmol) was slowly added to the the solution of (S)- 2-amino-9-[4-azido-2-(diisopropyl phosphonomethoxy)butyl]-6-chloropurine (0.6 g, 1.3 mmol) in 7 mL of anhydrous acetonitrile under nitrogen atmosphere. The solution was stirred at room temperature for 16 hours. The solvent was evaporated, and the residue was dried in vacuo. To the residue, water (2 mL) and acetone (15 mL) were added. The mixture was stirred at room temperature for 16 hours. The precipitate were filtered off and the solids collected were gently heated at reflux in 10 mL of 2N hydrochloric acid for 6 hours. The solvent was evaporated, and the product crystallized from water to provide 287 mg (62% yield) of the title compound as crystals. mp 245° C. dec.

$[\alpha]^{20}_D$ −0.45° (c 0.44 1N HCl)

$^1$H NMR (300 MHz, DMSO-d$_6$) δ 10.6 (bs, 1H, NH), 7.71 (s, 1H, H-8), 6.44 (br s, 2H, NH$_2$), 4.17 (dd, J=3.9, 14.2 Hz, 1H, H-1'), 4.02 (dd, J=4.7, 14.2 Hz, 1H, H-1'), 3.80–3.71 (m, 1H, H-2'), 3.66 (dd, J=9.3, 13.2 Hz, 1H, CH$_2$P), 3.51 (dd, J=9.8, 13.2 Hz, 1H, CH$_2$P), 3.46 (t, J=6.9 Hz, 2H, H-4'), 1.65–1.50, 1.50–1.38 (m, 2H, H-3').

$^{13}$C NMR (75 MHz, DMSO-d$_6$) δ 157.1, 154.0, 151.8, 138.6, 116.1, 77.0 (d, $^3J_{C,P}$=12 Hz, C-2'), 65.4 (d, $^1J_{C,P}$=162 Hz, CH$_2$P), 47.0 and 44.4 (C-1' and C-4'), 30.8 (C-3').

IR (KBr): 3500–2500 (OH, NH), 2106 (N$_3$), 1708 (C=O), 1102 (O—C), 1016, 950 (P—O), 772 (P—C).

UV (H$_2$O): 252 nm (ε=11,600)

MS (FAB) m/e:=359 (MH+).

Anal. Calcd for C$_9$H$_{15}$N$_6$O$_5$P·¼H$_2$O: C, 33.10; H, 4.31; N, 30.89. Found: C, 33.32; H, 4.16; N, 30.50.

EXAMPLE 12

(S)-9-[4-azido-2-(phosphonomethoxy)butyl]cytosine (S)-azidoethyl-PMEC

(S)-4-Azido-2-(diisopropyl phosphonomethoxy) butylcytosine (S)-4-Azido-2-O-(diisopropyl phosphonomethoxy)-1-O-methanesulfonyl-1,2-butanediol (1.0 g, 2.58 mmol) was mixed with cytosine (0.34 g, 3.10 mmol) and cesium carbonate (1.26 g, 3.87 mmol) in 10 mL of dry N',N'-dimethylformamide. The mixture was stirred at 95°–100° C. under nitrogen atmosphere for 6 hours. The mixture was allowed to cool to room temperature, and filtered. The solid was washed with methylene chloride. The filtrate was evaporated, and the residue was purified by flash chromatography on silica gel (methylene chloride:methanol=10:1 to 5:1) to give 440 mg (42% yield) of the title compound as a thick oil.

$^1$H NMR (300 MHz, CDCl$_3$) δ 7.43 (d, J=7.2 Hz, 1H, H-5), 5.70 (d, J=7.2 Hz, 1H, H-6), 4.75–4.60 (m, 2H, 2×POCH), 4.00 (dd, J=2.1, 12.9 Hz, 1H, H-1'), 3.82–3.69 (m, 3H, CH$_2$P, H-1' and H-2'), 3.63 (dd, J=9.5, 13.5 Hz, 1H, CH$_2$P), 3.52–3.38 (m, 2H, H-4'), 1.90–1.63 (m, 2H, H-3'), 1.31–1.27 (m, 12H,4×POCHCH$_3$).

$^{13}$C NMR (75 MHz, CDCl$_3$) δ 167.2, 157.5, 146.9, 95.3, 78.5 (d, $^3J_{C,P}$=5 Hz, C-2'), 71.6 (t, $^2J_{C,P}$=5 Hz, 2×POCH), 65.5 (d, $^1J_{C,P}$=171 Hz, CH2P), 52.5 (C-1'), 47.6 (C-4'), 31.3 (C-3'), 24.2 (d, $^3J_{C,P}$=4 Hz, POCHCH3).

MS (isobutane, DCI): m/e=403 (MH$^+$).

(S)-9-[4-azido-2-(phosphonomethoxy)butyl]cytosine (S)-azidoethyl-PMEC

To a solution of (S)-4-azido-2-(diisopropyl phosphonomethoxy)-butylcytosine (0.32 g, 0.98 mmol) in 5 mL of anhydrous acetonitrile, bromotrimethylsilane (1.49 g, 9.75 mmol) was slowly added under nitrogen atmosphere. The solution was stirred at room temperature for 14 hours. The solvent was evaporated, and the residue was dried in vacuo. To the residue, water (2 mL) and acetone (10 mL) were added. The mixture was stirred at room temperature for 20 hours. After the solvent was evaporated, the crude product purified by flash chromatography on reverse phase column (C18, water:methanol=10:1 to 5:1). The product collected was recrystallized from methanol and water to provide 194 mg (63% yield) of the title compound as crystals. mp 247° C. dec.

$[\alpha]^{20}_D$ +32.6° (c 0.32, H$_2$O).

$^1$H NMR (300 MHz, D$_2$O) δ 7.86 (d, J=7.7 Hz, 1H, H-5), 6.13 (d, J=7.7 Hz, 1H, H-6), 4.12 (d, J=11.5 Hz, 1H, H-1'), 3.88–3.75 (m, 2H, H-1' and H-2'), 3.68 (dd, J=9.6, 13.0 Hz, 1H, CH$_2$P), 3.54 (dd, J=9.7, 13.0 Hz, 1H, CH$_2$P), 3.49 (t, J=6.8 Hz, 2H, H-4'), 1.81 (q, J=6.6 Hz, 2H, H-3')

$^{13}$C NMR (75 MHz, D$_2$O) δ 164.2, 154.3, 153.7, 97.7, 80.6 (d, $^3J_{C,P}$=13 Hz, C-2'), 69.4 (d, $^1J_{C,P}$=158 Hz, CH$_2$P), 54.9 and 50.3 (C-1' and C-4'), 33.2 (C-3').

IR (KBr): 3500–2500 (OH, NH), 2100 (N$_3$), 1722 (C=O), 1680, 1658 (N=C, C=C), 1114, 1072, 930 (P—O), 770 (P—C).

UV (H$_2$O): 274 nm (ε=9,000),
198 nm (ε=20,200).

MS (FAB): m/e=319 (MH$^+$).

Anal. Calcd for C$_9$H$_{15}$N$_6$O$_5$P: C, 33.96; H, 4.75; N, 26.40. Found: C, 33.94; H, 4.65; N, 26.13.

What is claimed is:

1. A compound of the formula

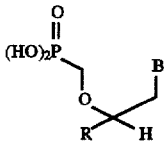

wherein

B is a purine base selected from the group consisting of adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, and 2,6-diaminopurine; R is aminomethyl, azidomethyl, alkenyl of 2 carbon atoms or alkynyl of 2 carbon atoms; the monoester, or diester of a C$_{1-5}$ alkanol, and the corresponding salt, hydrate, solvate, the R or S isomer and the racemic mixture RS thereof, with the proviso that when R is azidomethyl or aminomethyl then B is not adenine.

2. The compound of claim 1, wherein B is guanine or adenine; R is alkenyl of 2 carbon atoms or alkynyl of 2 carbon atoms.

3. The compound of claim 1, wherein B is guanine or adenine; R is —CH$_2$NH$_2$ and said compound is the R or S isomer or its racemic mixture thereof.

4. The compound which is (RS) or (R) or (S)-9-[2-(phosphonomethoxy)-3-butenyl]guanine.

5. The compound of claim 1 wherein B is 2,6-diaminopurine.

6. The compound of claim 1 wherein B is guanine.

7. The compound of claim 1 wherein B is 2-aminopurine.

8. The compound of claim 1 wherein B is adenine.

9. (S)-2-amino-9-[3-azido-2-(diisopropylphosphonomethoxy)propyl]-6-chloropurine.

10. (S)-2-amino-6-chloro-9-[2-(diisopropyl phosphonomethoxy-3-butenyl]purine.

11. The compound of claim 1 wherein the compound is the R isomer.

12. The compound of claim 1 wherein R is —CH=CH$_2$.

13. The compound of claim 1 wherein the compound is the R isomer and wherein R is —CH=CH$_2$.

14. The compound of claim 12 wherein B is adenine.

* * * * *